US011965004B2

(12) United States Patent
Brown et al.

(10) Patent No.: US 11,965,004 B2
(45) Date of Patent: *Apr. 23, 2024

(54) MOLECULAR GUIDE SYSTEM PEPTIDES AND USES THEREOF

(71) Applicant: SRI INTERNATIONAL, Menlo Park, CA (US)

(72) Inventors: Kathlynn C. Brown, Staunton, VA (US); Nathan Collins, Menlo Park, CA (US); Shunzi "Susan" Li, Harrisonburg, VA (US); Curtis Allred, Menlo Park, CA (US); Keen Chung, Menlo Park, CA (US); Michael McGuire, Menlo Park, CA (US)

(73) Assignee: SRI International, Menlo Park, CA (US)

( * ) Notice: Subject to any disclaimer, the term of this patent is extended or adjusted under 35 U.S.C. 154(b) by 520 days.

This patent is subject to a terminal disclaimer.

(21) Appl. No.: 16/629,799

(22) PCT Filed: Jul. 10, 2018

(86) PCT No.: PCT/US2018/041403
§ 371 (c)(1),
(2) Date: Jan. 9, 2020

(87) PCT Pub. No.: WO2019/014190
PCT Pub. Date: Jan. 17, 2019

(65) Prior Publication Data
US 2022/0227823 A1    Jul. 21, 2022

Related U.S. Application Data

(60) Provisional application No. 62/530,633, filed on Jul. 10, 2017.

(51) Int. Cl.
*C07K 14/47* (2006.01)
*A61K 47/64* (2017.01)
*A61P 35/00* (2006.01)
*C07K 16/28* (2006.01)
*A61K 38/00* (2006.01)

(52) U.S. Cl.
CPC .......... *C07K 14/4702* (2013.01); *A61K 47/64* (2017.08); *A61P 35/00* (2018.01); *C07K 16/2803* (2013.01); *A61K 38/00* (2013.01)

(58) Field of Classification Search
CPC ...... C07K 14/4702; A61K 47/64; A61P 35/00
See application file for complete search history.

(56) References Cited

U.S. PATENT DOCUMENTS

| | | | | |
|---|---|---|---|---|
| 8,241,623 B1 * | 8/2012 | Bermudes | ............ | C12N 15/74 424/93.4 |
| 8,524,220 B1 * | 9/2013 | Bermudes | ................ | C12N 9/22 424/94.63 |
| 8,623,350 B1 * | 1/2014 | Bermudes | ............ | C07K 14/245 424/93.4 |
| 9,068,187 B1 * | 6/2015 | Bermudes | ................ | C07K 7/06 |
| 9,200,289 B1 * | 12/2015 | Bermudes | ............ | C07K 14/81 |
| 2005/0288492 A1 * | 12/2005 | Rabbitts | ................. | A61P 35/00 536/23.53 |
| 2006/0239968 A1 | 10/2006 | Arap et al. | | |
| 2008/0206136 A1 | 8/2008 | Greene et al. | | |
| 2009/0110662 A1 * | 4/2009 | Breitenkamp | ......... | A61K 47/62 548/506 |
| 2010/0247589 A1 * | 9/2010 | Fahnestock | ............. | A61K 8/25 424/49 |
| 2012/0141478 A1 | 6/2012 | Coupade | | |
| 2012/0208742 A1 * | 8/2012 | Primiano | ............... | C12N 15/87 977/773 |
| 2012/0283410 A1 * | 11/2012 | Mirosevich | ............. | C07K 7/06 530/321 |
| 2014/0022045 A1 * | 1/2014 | Jang | ...................... | G11C 19/00 337/64 |
| 2014/0094404 A1 | 4/2014 | Corrales et al. | | |
| 2015/0071862 A1 * | 3/2015 | Sabatino | ............. | A61K 47/549 424/9.61 |

(Continued)

FOREIGN PATENT DOCUMENTS

| | | |
|---|---|---|
| AU | 2018301804 | 7/2018 |
| CN | 101724073 A | 6/2010 |
| CN | 2018800556748 | 6/2020 |

(Continued)

OTHER PUBLICATIONS

European Search Report dated Apr. 19, 2022 by the European Patent Office for EP Application EP18831318.3 filed on Jul. 10, 2018 and published as EP3652196A0 on May 20, 2020, 10 pgs.

International Search Report and Written Opinion dated Nov. 8, 2018 by the International Searching Authority for International Application No. PCT/US2018/041403, filed on Jul. 10, 2018 and published as WO/2019/014190 on Jan. 17, 2019, 12 pgs.

International Preliminary Report on Patentability dated Jan. 14, 2020 by the International Searching Authority for International Application No. PCT/US2018/041403, filed on Jul. 10, 2018 and published as WO/2019/014190 on Jan. 17, 2019, 7 pgs.

(Continued)

*Primary Examiner* — Amber D Steele
(74) *Attorney, Agent, or Firm* — Dicke, Billig & Czaja, PLLC

(57) ABSTRACT

Disclosed are compositions comprising an antibody conjugated to one or more molecular guidance system (MGS) peptides. Disclosed are methods of treating a subject in need thereof comprising administering to the subject in need thereof an effective amount of an antibody conjugated to one or more MGS peptides, wherein the antibody targets an intracellular target involved in the disease process. Disclosed are methods of targeting an intracellular target comprising administering an antibody conjugated to one or more MGS peptides, wherein the antibody targets an intracellular target.

13 Claims, 26 Drawing Sheets
Specification includes a Sequence Listing.

(56) References Cited

U.S. PATENT DOCUMENTS

2015/0203557 A1 7/2015 Debinski et al.
2016/0310607 A1* 10/2016 Ryves .................. C12N 15/62

FOREIGN PATENT DOCUMENTS

| EP | 18831318.3 | 7/2020 |
| JP | 2020501210 | 12/2020 |
| WO | 2004003170 A2 | 1/2004 |
| WO | WO 2004/003170 * | 1/2004 |
| WO | WO-2012/177868 A1 | 12/2012 |
| WO | WO-2016/022597 A1 | 2/2016 |
| WO | PCT/US2018/041403 | 7/2018 |

OTHER PUBLICATIONS

Lim et al. "A Cancer Specific Cell-Penetrating Peptide, BR2, for the Efficient Delivery of an scFv into Cancer Cells", Jun. 1, 2013, PLOS One, vol. 8, No. 6, p. e66084.

Mcguire et al. Identification and Characterization of a Suite of Tumor Targeting Peptides for non-Small Cell Lung Cancer. Scientific Reports, Mar. 27, 2014, vol. 4, Article 4480, pp. 1-11.

Umlauf et al., "Identification of a Novel Lysosomal Trafficking Peptide using Phage Display Biopanning Coupled with Endocytic Selection Pressure", Bioconjugate Chemistry, vol. 25, No. 10, Oct. 15, 2014 (Oct. 15, 2014), pp. 1829-1837.

U.S. Appl. No. 62/530,633, filed Jul. 10, 2017, Kathlynn C. Brown.

Lim et al., "A Cancer Specific Cell-Penetrating Peptide, BR2, for the Efficient Delivery of an scFv into Cancer Cells", PloS One, Issue 6, vol. 8, Jun. 11, 2013, pp. 1-11.

* cited by examiner

| MGS Name | Selected Sequence | Optimized Sequence | Optimal Valency | Cellular Location | In Vivo Targeting |
|---|---|---|---|---|---|
| | | Carcinomas and Solid Tumors | | | |
| MGS_H1299.1 | VSQTMRQTAVPLLWFWTGSL | | | Intracellular | |
| MGS_1299.2 | YAAWPASGAWTGTAPCSAGT | MGS_1299.2 V4 CH3CO-YAAWPASGAWT-PEG$_{11}$-C-NH$_2$ | Dimer | Lysosome | Yes |
| MGS_1299.3 | LQWRRDDNVHNFGVWARYRL | MGS_1299.3 V2 CH3CO-LQWRRNFGVWARYRL-PEG$_{11}$-C-NH$_2$ | Dimer | Autophagasome | Yes |
| MGS_H2009.1 | RGDLATLRQLAQEDGVVGVR | MGS_2009.1 V4 CH3CO-RGDLATLRQL-PEG$_{11}$-YC-NH$_2$ | Dimer | Golgi | Yes |
| | | MGS_H2009.1 V5 CH3CO-d(Leu)-RGDLATLRQL-PEG$_{11}$-YC-NH$_2$ | Dimer | | |
| MGS_H2009.2 | EHPWFNMWSWATQVQE | | | Lysosome | |
| MGS_H2009.3 | YPGSPTQYPSSMHEYHSSSE | | | Lysosome | |
| MGS_H2009.4 | AHTIDDEWASYHMQQWNSPP | | | Golgi/ER | |
| MGS_H2009.5 | FEEFYSRQSNTIPYPQQYKG | | | ER/Lysosome | |
| MGS_HCC15.1 | ATEPRKQYATPRVFWTDAPG | MGS_HCC15.1 V4 CH3CO-LQWRRNFGVWARYRL-PEG$_{11}$-C-NH$_2$ | Dimer | Lysosome | Yes |
| MGS_HCC15.2 | FHAVPQSFYTAP | MGS_HCC15.2 V8 CH3CO-FHAVPQSFYT-PEG$_{11}$-C-NH$_2$ | Monomer | Lysosome | Yes |
| | | MGS_HCC15.2 V9 CH3CO-FHAVPQSFYT-PEG$_{11}$-C-NH$_2$ | Dimer | | |
| MGS_H460.1 | EAMNSAEQSAAVVQWEKRRI | | | Plasma Membrane | Yes |
| MGS_A549.1 | MTVCNASQRQAHAQATAVSL | | | Intracellular | |
| MGS_MCF7.1 | LTVHGRGPEYNPSWNRRAFP | | | Intracellular | |
| MGS_H1993.1 | SVEYWGERMYDVMESLGFS | | | Lysosome | |
| MGS_H1993.2 | FAAKRAEWWDPGGLWDAVWN | | | Intracellular | |
| MGS_H1993.3 | QEALEEWFWKMMPWSGPSGQ | | | Intracellular | |
| MGS_H1993.4 | TWTDFGQWPWPFGAEGTRAF | | | Pre-mitotic cells only | |
| MGS_H1993.5 | MDGATWWTQLDPLLVWEGET | | | Intracellular | |
| MGS_H1993.6 | SADWFQGPAEWLLEGWMGPL | | | Intracellular | |
| MGS_HCC95.1 | MRGQTGKLPTEHFTDTGVAF | | | | |
| MGS_H1155.1 | MTGKAAAPHQEDRHANGLEQ | | | | |

FIG. 18

| MGS | EC50 (nM) | Saturation (molecules) | Molecules internalized, 6 H | t₁/₂ (mins) | Specificity | EC50 (nM) | Saturation (molecules) | Molecules internalized, 6 H | t₁/₂ (mins) | Specificity |
|---|---|---|---|---|---|---|---|---|---|---|
| H2009.1V4 | 1.8 | 70500 ± 13500 | 223100 ± 11500 | Linear | 230 | 2.7 | 24900 | 105400 ± 42900 | Linear | 50 |
| H1299.2V4 | 0.72 | 68200 ± 3030 | 49560 ± 2230 | 13 | 560 | 0.89 | 99300 ± 9640 | 97100 ± 4230 | 11 | 1100 |
| HCC15.1V4 | 7.2 | 78000 ± 8080 | 31900 ± 2500 | 66 | 310 | 7.0 | 103300 ± 11910 | 87300 ± 3020 | 42 | 450 |
| HCC15.2V9 | 6.8 | 53700 ± 6750 | 32100 ± 2990 | 27 | 330 | 3.9 | 99100 ± 11600 | 89980 ± 3650 | 19 | 860 |

| MGS | EC50 (nM) | Saturation (molecules) | Molecules internalized, 6 H | t₁/₂ (mins) | Specificity | EC50 (nM) | Saturation (molecules) | Molecules internalized, 6 H | t₁/₂ (mins) | Specificity |
|---|---|---|---|---|---|---|---|---|---|---|
| H2009.1V4 | 1.2 | 57400 ± 18300 | 117800 ± 3400 | Linear | 230 | NB | NB | — | — | — |
| H1299.2V4 | 1.2 | 141600 ± 28210 | 134300 ± 6300 | 12 | 2300 | 1.4 | 112800 ± 15500 | 125500 ± 5430 | 37 | 1400 |
| HCC15.1V4 | 4.1 | 132700 ± 23700 | 140300 ± 7160 | 21 | 10002 | 5.6 | 86000 ± 6900 | 117200 ± 7780 | 55 | 800 |
| HCC15.2V9 | 4.0 | 102200 ± 14600 | 68200 ± 3300 | 26 | 1600 | 5.7 | 67400 ± 9300 | 116300 ± 3730 | 69 | 980 |

1. Average number of MGS molecules internalized per cell at saturation concentration of 1 H
2. Average number of molecules internalized at 6 H with constant incubation of 20 nM MGS
3. Ratio of MGS uptake on indicated cancer cell line vs. a non-transformed, immortalized normal human bronchial epithelial cell line (HBEC)

FIG. 25 the foregoing general description and the following detailed

```
                         SEQUENCE LISTING

<160> NUMBER OF SEQ ID NOS: 84

<210> SEQ ID NO 1
   <211> LENGTH: 12
   <212> TYPE: PRT
   <213> ORGANISM: Artificial Sequence
   <220> FEATURE:
   <223> OTHER INFORMATION: Synthetic construct

<400> SEQUENCE: 1

Phe His Ala Val Pro Gln Ser Phe Tyr Thr Ala Pro
   1               5                   10

<210> SEQ ID NO 2
   <211> LENGTH: 11
   <212> TYPE: PRT
   <213> ORGANISM: Artificial Sequence
   <220> FEATURE:
   <223> OTHER INFORMATION: Synthetic construct

<400> SEQUENCE: 2

Phe His Ala Val Pro Gln Ser Phe Tyr Thr Ala
   1               5                   10

<210> SEQ ID NO 3
   <211> LENGTH: 10
   <212> TYPE: PRT
   <213> ORGANISM: Artificial Sequence
   <220> FEATURE:
   <223> OTHER INFORMATION: Synthetic Construct

<400> SEQUENCE: 3

Phe His Ala Val Pro Gln Ser Phe Tyr Thr
   1               5                   10

<210> SEQ ID NO 4
   <211> LENGTH: 20
   <212> TYPE: PRT
   <213> ORGANISM: Artificial Sequence
   <220> FEATURE:
   <223> OTHER INFORMATION: Synthetic Construct

<400> SEQUENCE: 4

Val Ser Gln Thr Met Arg Gln Thr Ala Val Pro Leu Leu Trp Phe Trp
   1               5                   10                  15

Thr Gly Ser Leu
               20

<210> SEQ ID NO 5
   <211> LENGTH: 20
   <212> TYPE: PRT
```

<213> ORGANISM: Artificial Sequence
<220> FEATURE:
<223> OTHER INFORMATION: Synthetic construct

<400> SEQUENCE: 5

Tyr Ala Ala Trp Pro Ala Ser Gly Ala Trp Thr Gly Thr Ala Pro Cys
1               5                   10                  15

Ser Ala Gly Thr
            20

<210> SEQ ID NO 6
<211> LENGTH: 11
<212> TYPE: PRT
<213> ORGANISM: Artificial Sequence
<220> FEATURE:
<223> OTHER INFORMATION: Synthetic construct

<400> SEQUENCE: 6

Tyr Ala Ala Trp Pro Ala Ser Gly Ala Trp Thr
1               5                   10

<210> SEQ ID NO 7
<211> LENGTH: 19
<212> TYPE: PRT
<213> ORGANISM: Artificial Sequence
<220> FEATURE:
<223> OTHER INFORMATION: Synthetic construct

<400> SEQUENCE: 7

Arg Gly Asp Leu Ala Thr Leu Arg Gln Leu Ala Gln Glu Asp Gly Val
1               5                   10                  15

Val Gly Val

<210> SEQ ID NO 8
<211> LENGTH: 11
<212> TYPE: PRT
<213> ORGANISM: Artificial Sequence
<220> FEATURE:
<223> OTHER INFORMATION: Synthetic construct

<400> SEQUENCE: 8

Leu Arg Gly Asp Leu Ala Thr Leu Arg Gln Leu
1               5                   10

<210> SEQ ID NO 9
<211> LENGTH: 20
<212> TYPE: PRT
<213> ORGANISM: Artificial Sequence
<220> FEATURE:
<223> OTHER INFORMATION: Synthetic construct

<400> SEQUENCE: 9

Glu Ala Met Asn Ser Ala Glu Gln Ser Ala Ala Val Val Gln Trp Glu
1               5                   10                  15

Lys Arg Arg Ile
            20

<210> SEQ ID NO 10
<211> LENGTH: 20
<212> TYPE: PRT
<213> ORGANISM: Artificial Sequence
<220> FEATURE:
<223> OTHER INFORMATION: Synthetic construct

<400> SEQUENCE: 10

Ala Thr Glu Pro Arg Lys Gln Tyr Ala Thr Pro Arg Val Phe Trp Thr
1               5                   10                  15

Asp Ala Pro Gly
            20

<210> SEQ ID NO 11
<211> LENGTH: 20
<212> TYPE: PRT
<213> ORGANISM: Artificial Sequence
<220> FEATURE:
<223> OTHER INFORMATION: Synthetic construct

<400> SEQUENCE: 11

Met Thr Val Cys Asn Ala Ser Gln Arg Gln His Ala Gln Ala Thr
1               5                   10                  15

Ala Val Ser Leu
            20

<210> SEQ ID NO 12
<211> LENGTH: 20
<212> TYPE: PRT
<213> ORGANISM: Artificial Sequence
<220> FEATURE:
<223> OTHER INFORMATION: Synthetic construct

<400> SEQUENCE: 12

Met Arg Gly Gln Thr Gly Lys Leu Pro Thr Glu His Phe Thr Asp Thr
1               5                   10                  15

Gly Val Ala Phe
            20

<210> SEQ ID NO 13
<211> LENGTH: 20
<212> TYPE: PRT
<213> ORGANISM: Artificial Sequence
<220> FEATURE:
<223> OTHER INFORMATION: Synthetic construct

<400> SEQUENCE: 13

Met Thr Gly Lys Ala Ala Ala Pro His Gln Glu Asp Arg His Ala Asn
1               5                   10                  15

Gly Leu Glu Gln
            20

<210> SEQ ID NO 14
<211> LENGTH: 19
<212> TYPE: PRT
<213> ORGANISM: Artificial Sequence
<220> FEATURE:
<223> OTHER INFORMATION: Synthetic construct

<400> SEQUENCE: 14

Thr Asn Ser Cys Arg Gly Asp Trp Leu Cys Asp Ala Val Pro Glu Lys
1               5                   10                  15

Ala Arg Val

<210> SEQ ID NO 15
<211> LENGTH: 16
<212> TYPE: PRT
<213> ORGANISM: Artificial Sequence
<220> FEATURE:
<223> OTHER INFORMATION: Synthetic construct

<400> SEQUENCE: 15

```
Glu His Pro Trp Phe Asn Met Trp Ser Trp Ala Thr Gln Val Gln Glu
1               5                   10                  15
```

<210> SEQ ID NO 16
<211> LENGTH: 20
<212> TYPE: PRT
<213> ORGANISM: Artificial Sequence
<220> FEATURE:
<223> OTHER INFORMATION: Synthetic construct

<400> SEQUENCE: 16

```
Tyr Pro Gly Ser Pro Thr Gln Tyr Pro Ser Ser Met His Glu Tyr His
1               5                   10                  15

Ser Ser Ser Glu
            20
```

<210> SEQ ID NO 17
<211> LENGTH: 20
<212> TYPE: PRT
<213> ORGANISM: Artificial Sequence
<220> FEATURE:
<223> OTHER INFORMATION: Synthetic construct

<400> SEQUENCE: 17

```
Ala His Thr Ile Asp Asp Glu Trp Ala Ser Tyr His Met Gln Gln Trp
1               5                   10                  15

Asn Ser Pro Pro
            20
```

<210> SEQ ID NO 18
<211> LENGTH: 20
<212> TYPE: PRT
<213> ORGANISM: Artificial Sequence
<220> FEATURE:
<223> OTHER INFORMATION: Synthetic construct

<400> SEQUENCE: 18

```
Phe Glu Glu Phe Tyr Ser Arg Gln Ser Asn Thr Ile Pro Tyr Pro Gln
1               5                   10                  15

Gln Tyr Lys Gly
            20
```

<210> SEQ ID NO 19
<211> LENGTH: 20
<212> TYPE: PRT
<213> ORGANISM: Artificial Sequence
<220> FEATURE:
<223> OTHER INFORMATION: Synthetic construct

<400> SEQUENCE: 19

```
Thr His Gly Asn Lys His Gln Ser Trp Thr Tyr Pro Ser Glu Ile Asn
1               5                   10                  15

His Lys Asn Tyr
            20
```

<210> SEQ ID NO 20
<211> LENGTH: 21
<212> TYPE: PRT
<213> ORGANISM: Artificial Sequence
<220> FEATURE:
<223> OTHER INFORMATION: Synthetic construct

<400> SEQUENCE: 20

```
Asn Leu Ala Asp Thr Trp Thr Gln Thr Gln Gln His Asp Phe His Val
1               5                   10                  15
```

```
Leu Arg Gly Thr Arg
            20

<210> SEQ ID NO 21
<211> LENGTH: 16
<212> TYPE: PRT
<213> ORGANISM: Artificial Sequence
<220> FEATURE:
<223> OTHER INFORMATION: Synthetic construct

<400> SEQUENCE: 21

Gly Tyr Ser Trp Trp Gln Pro Asn Trp Pro Ser Ser Thr Trp Asp Thr
1               5                   10                  15

<210> SEQ ID NO 22
<211> LENGTH: 19
<212> TYPE: PRT
<213> ORGANISM: Artificial Sequence
<220> FEATURE:
<223> OTHER INFORMATION: Synthetic construct

<400> SEQUENCE: 22

Glu His Pro Trp Phe Asn Met Trp Ser Trp Ala Thr Gln Val Gln Glu
1               5                   10                  15

Lys Lys Lys

<210> SEQ ID NO 23
<211> LENGTH: 20
<212> TYPE: PRT
<213> ORGANISM: Artificial Sequence
<220> FEATURE:
<223> OTHER INFORMATION: Synthetic construct

<400> SEQUENCE: 23

Asn Leu Ala Asp Thr Trp Thr Gln Thr Gln Gln His Asp Phe His Val
1               5                   10                  15

Leu Arg Gly Thr
            20

<210> SEQ ID NO 24
<211> LENGTH: 20
<212> TYPE: PRT
<213> ORGANISM: Artificial Sequence
<220> FEATURE:
<223> OTHER INFORMATION: Synthetic construct

<400> SEQUENCE: 24

Ser Val Glu Tyr Trp Gly Glu Arg Met Tyr Tyr Asp Val Met Glu Ser
1               5                   10                  15

Leu Gly Phe Ser
            20

<210> SEQ ID NO 25
<211> LENGTH: 20
<212> TYPE: PRT
<213> ORGANISM: Artificial Sequence
<220> FEATURE:
<223> OTHER INFORMATION: Synthetic construct

<400> SEQUENCE: 25

Phe Ala Ala Lys Arg Ala Glu Trp Trp Asp Pro Gly Gln Leu Trp Asp
1               5                   10                  15

Ala Val Trp Asn
            20
```

```
<210> SEQ ID NO 26
<211> LENGTH: 20
<212> TYPE: PRT
<213> ORGANISM: Artificial Sequence
<220> FEATURE:
<223> OTHER INFORMATION: Synthetic construct

<400> SEQUENCE: 26

Gln Glu Ala Leu Glu Glu Trp Phe Trp Lys Met Met Pro Trp Ser Gly
1               5                   10                  15

Pro Ser Gly Gln
            20

<210> SEQ ID NO 27
<211> LENGTH: 20
<212> TYPE: PRT
<213> ORGANISM: Artificial Sequence
<220> FEATURE:
<223> OTHER INFORMATION: Synthetic construct

<400> SEQUENCE: 27

Thr Trp Thr Asp Phe Gly Gln Trp Pro Trp Pro Phe Gly Ala Glu Gly
1               5                   10                  15

Thr Arg Ala Phe
            20

<210> SEQ ID NO 28
<211> LENGTH: 20
<212> TYPE: PRT
<213> ORGANISM: Artificial Sequence
<220> FEATURE:
<223> OTHER INFORMATION: Synthetic construct

<400> SEQUENCE: 28

Met Asp Gly Ala Thr Trp Trp Thr Gln Leu Asp Pro Leu Leu Val Trp
1               5                   10                  15

Glu Gly Glu Thr
            20

<210> SEQ ID NO 29
<211> LENGTH: 20
<212> TYPE: PRT
<213> ORGANISM: Artificial Sequence
<220> FEATURE:
<223> OTHER INFORMATION: Synthetic construct

<400> SEQUENCE: 29

Ser Ala Asp Trp Phe Gln Gly Pro Ala Glu Trp Leu Leu Glu Gly Trp
1               5                   10                  15

Met Gly Pro Leu
            20

<210> SEQ ID NO 30
<211> LENGTH: 20
<212> TYPE: PRT
<213> ORGANISM: Artificial Sequence
<220> FEATURE:
<223> OTHER INFORMATION: Synthetic construct

<400> SEQUENCE: 30

Leu Gln Trp Arg Arg Asp Asp Asn Val His Asn Phe Gly Val Trp Ala
1               5                   10                  15

Arg Tyr Arg Leu
```

```
                    20

<210> SEQ ID NO 31
<211> LENGTH: 15
<212> TYPE: PRT
<213> ORGANISM: Artificial Sequence
<220> FEATURE:
<223> OTHER INFORMATION: Synthetic construct

<400> SEQUENCE: 31

Leu Gln Trp Arg Arg Asn Phe Gly Val Trp Ala Arg Tyr Arg Leu
1               5                   10                  15

<210> SEQ ID NO 32
<211> LENGTH: 20
<212> TYPE: PRT
<213> ORGANISM: Artificial Sequence
<220> FEATURE:
<223> OTHER INFORMATION: Synthetic construct

<400> SEQUENCE: 32

Ala Thr Glu Pro Arg Lys Gln Tyr Ala Thr Pro Arg Val Phe Trp Thr
1               5                   10                  15

Asp Ala Pro Gly
            20

<210> SEQ ID NO 33
<211> LENGTH: 11
<212> TYPE: PRT
<213> ORGANISM: Artificial Sequence
<220> FEATURE:
<223> OTHER INFORMATION: Synthetic construct

<400> SEQUENCE: 33

Lys Gln Tyr Ala Thr Pro Arg Val Phe Trp Thr
1               5                   10

<210> SEQ ID NO 34
<211> LENGTH: 20
<212> TYPE: PRT
<213> ORGANISM: Artificial Sequence
<220> FEATURE:
<223> OTHER INFORMATION: Synthetic construct

<400> SEQUENCE: 34

Val Ser Gln Thr Met Arg Gln Thr Ala Val Pro Leu Leu Trp Phe Trp
1               5                   10                  15

Thr Gly Ser Leu
            20

<210> SEQ ID NO 35
<211> LENGTH: 20
<212> TYPE: PRT
<213> ORGANISM: Artificial Sequence
<220> FEATURE:
<223> OTHER INFORMATION: Synthetic construct

<400> SEQUENCE: 35

Tyr Ala Ala Trp Pro Ala Ser Gly Ala Trp Thr Gly Thr Ala Pro Cys
1               5                   10                  15

Ser Ala Gly Thr
            20

<210> SEQ ID NO 36
<211> LENGTH: 20
```

-continued

```
<212> TYPE: PRT
<213> ORGANISM: Artificial Sequence
<220> FEATURE:
<223> OTHER INFORMATION: Synthetic construct

<400> SEQUENCE: 36

Leu Gln Trp Arg Arg Asp Asp Asn Val His Asn Phe Gly Val Trp Ala
1               5                   10                  15

Arg Tyr Arg Leu
            20

<210> SEQ ID NO 37
<211> LENGTH: 20
<212> TYPE: PRT
<213> ORGANISM: Artificial Sequence
<220> FEATURE:
<223> OTHER INFORMATION: Synthetic construct

<400> SEQUENCE: 37

Arg Gly Asp Leu Ala Thr Leu Arg Gln Leu Ala Gln Glu Asp Gly Val
1               5                   10                  15

Val Gly Val Arg
            20

<210> SEQ ID NO 38
<211> LENGTH: 16
<212> TYPE: PRT
<213> ORGANISM: Artificial Sequence
<220> FEATURE:
<223> OTHER INFORMATION: Synthetic construct

<400> SEQUENCE: 38

Glu His Pro Trp Phe Asn Met Trp Ser Trp Ala Thr Gln Val Gln Glu
1               5                   10                  15

<210> SEQ ID NO 39
<211> LENGTH: 20
<212> TYPE: PRT
<213> ORGANISM: Artificial Sequence
<220> FEATURE:
<223> OTHER INFORMATION: Synthetic construct

<400> SEQUENCE: 39

Tyr Pro Gly Ser Pro Thr Gln Tyr Pro Ser Ser Met His Glu Tyr His
1               5                   10                  15

Ser Ser Ser Glu
            20

<210> SEQ ID NO 40
<211> LENGTH: 20
<212> TYPE: PRT
<213> ORGANISM: Artificial Sequence
<220> FEATURE:
<223> OTHER INFORMATION: Synthetic construct

<400> SEQUENCE: 40

Ala His Thr Ile Asp Asp Glu Trp Ala Ser Tyr His Met Gln Gln Trp
1               5                   10                  15

Asn Ser Pro Pro
            20

<210> SEQ ID NO 41
<211> LENGTH: 20
<212> TYPE: PRT
<213> ORGANISM: Artificial Sequence
```

```
<220> FEATURE:
<223> OTHER INFORMATION: Synthetic construct

<400> SEQUENCE: 41

Phe Glu Glu Phe Tyr Ser Arg Gln Ser Asn Thr Ile Pro Tyr Pro Gln
1               5                   10                  15

Gln Tyr Lys Gly
            20

<210> SEQ ID NO 42
<211> LENGTH: 20
<212> TYPE: PRT
<213> ORGANISM: Artificial Sequence
<220> FEATURE:
<223> OTHER INFORMATION: Synthetic construct

<400> SEQUENCE: 42

Ala Thr Glu Pro Arg Lys Gln Tyr Ala Thr Pro Arg Val Phe Trp Thr
1               5                   10                  15

Asp Ala Pro Gly
            20

<210> SEQ ID NO 43
<211> LENGTH: 12
<212> TYPE: PRT
<213> ORGANISM: Artificial Sequence
<220> FEATURE:
<223> OTHER INFORMATION: Synthetic construct

<400> SEQUENCE: 43

Phe His Ala Val Pro Gln Ser Phe Tyr Thr Ala Pro
1               5                   10

<210> SEQ ID NO 44
<211> LENGTH: 20
<212> TYPE: PRT
<213> ORGANISM: Artificial Sequence
<220> FEATURE:
<223> OTHER INFORMATION: Synthetic construct

<400> SEQUENCE: 44

Glu Ala Met Asn Ser Ala Glu Gln Ser Ala Ala Val Val Gln Trp Glu
1               5                   10                  15

Lys Arg Arg Ile
            20

<210> SEQ ID NO 45
<211> LENGTH: 20
<212> TYPE: PRT
<213> ORGANISM: Artificial Sequence
<220> FEATURE:
<223> OTHER INFORMATION: Synthetic construct

<400> SEQUENCE: 45

Met Thr Val Cys Asn Ala Ser Gln Arg Gln His Ala Gln Ala Thr
1               5                   10                  15

Ala Val Ser Leu
            20

<210> SEQ ID NO 46
<211> LENGTH: 20
<212> TYPE: PRT
<213> ORGANISM: Artificial Sequence
<220> FEATURE:
<223> OTHER INFORMATION: Synthetic construct
```

```
<400> SEQUENCE: 46

Leu Thr Val His Gly Arg Gly Pro Glu Tyr Asn Pro Ser Trp Asn Arg
1               5                   10                  15

Arg Ala Phe Pro
            20

<210> SEQ ID NO 47
<211> LENGTH: 20
<212> TYPE: PRT
<213> ORGANISM: Artificial Sequence
<220> FEATURE:
<223> OTHER INFORMATION: Synthetic construct

<400> SEQUENCE: 47

Ser Val Glu Tyr Trp Gly Glu Arg Met Tyr Tyr Asp Val Met Glu Ser
1               5                   10                  15

Leu Gly Phe Ser
            20

<210> SEQ ID NO 48
<211> LENGTH: 20
<212> TYPE: PRT
<213> ORGANISM: Artificial Sequence
<220> FEATURE:
<223> OTHER INFORMATION: Synthetic construct

<400> SEQUENCE: 48

Phe Ala Ala Lys Arg Ala Glu Trp Trp Asp Pro Gly Gln Leu Trp Asp
1               5                   10                  15

Ala Val Trp Asn
            20

<210> SEQ ID NO 49
<211> LENGTH: 20
<212> TYPE: PRT
<213> ORGANISM: Artificial Sequence
<220> FEATURE:
<223> OTHER INFORMATION: Synthetic construct

<400> SEQUENCE: 49

Gln Glu Ala Leu Glu Glu Trp Phe Trp Lys Met Met Pro Trp Ser Gly
1               5                   10                  15

Pro Ser Gly Gln
            20

<210> SEQ ID NO 50
<211> LENGTH: 20
<212> TYPE: PRT
<213> ORGANISM: Artificial Sequence
<220> FEATURE:
<223> OTHER INFORMATION: Synthetic construct

<400> SEQUENCE: 50

Thr Trp Thr Asp Phe Gly Gln Trp Pro Trp Pro Phe Gly Ala Glu Gly
1               5                   10                  15

Thr Arg Ala Phe
            20

<210> SEQ ID NO 51
<211> LENGTH: 20
<212> TYPE: PRT
<213> ORGANISM: Artificial Sequence
<220> FEATURE:
```

<223> OTHER INFORMATION: Synthetic construct

<400> SEQUENCE: 51

Met Asp Gly Ala Thr Trp Trp Thr Gln Leu Asp Pro Leu Leu Val Trp
1               5                   10                  15

Glu Gly Glu Thr
            20

<210> SEQ ID NO 52
<211> LENGTH: 20
<212> TYPE: PRT
<213> ORGANISM: Artificial Sequence
<220> FEATURE:
<223> OTHER INFORMATION: Synthetic construct

<400> SEQUENCE: 52

Ser Ala Asp Trp Phe Gln Gly Pro Ala Glu Trp Leu Leu Glu Gly Trp
1               5                   10                  15

Met Gly Pro Leu
            20

<210> SEQ ID NO 53
<211> LENGTH: 20
<212> TYPE: PRT
<213> ORGANISM: Artificial Sequence
<220> FEATURE:
<223> OTHER INFORMATION: Synthetic construct

<400> SEQUENCE: 53

Met Arg Gly Gln Thr Gly Lys Leu Pro Thr Glu His Phe Thr Asp Thr
1               5                   10                  15

Gly Val Ala Phe
            20

<210> SEQ ID NO 54
<211> LENGTH: 20
<212> TYPE: PRT
<213> ORGANISM: Artificial Sequence
<220> FEATURE:
<223> OTHER INFORMATION: Synthetic construct

<400> SEQUENCE: 54

Met Thr Gly Lys Ala Ala Ala Pro His Gln Glu Asp Arg His Ala Asn
1               5                   10                  15

Gly Leu Glu Gln
            20

<210> SEQ ID NO 55
<211> LENGTH: 20
<212> TYPE: PRT
<213> ORGANISM: Artificial Sequence
<220> FEATURE:
<223> OTHER INFORMATION: Synthetic construct

<400> SEQUENCE: 55

Met Glu Lys Leu Pro Leu Ser Lys Thr Gly Arg Thr Val Ser Glu Gly
1               5                   10                  15

Val Ser Pro Pro
            20

<210> SEQ ID NO 56
<211> LENGTH: 19
<212> TYPE: PRT
<213> ORGANISM: Artificial Sequence

```
<220> FEATURE:
<223> OTHER INFORMATION: Synthetic construct

<400> SEQUENCE: 56

Thr Asn Ser Cys Arg Gly Asp Trp Leu Cys Asp Ala Val Pro Glu Lys
1               5                   10                  15

Ala Arg Val

<210> SEQ ID NO 57
<211> LENGTH: 20
<212> TYPE: PRT
<213> ORGANISM: Artificial Sequence
<220> FEATURE:
<223> OTHER INFORMATION: Synthetic construct

<400> SEQUENCE: 57

Ser Ala Lys Thr Ala Val Ser Gln Arg Val Trp Leu Pro Ser His Arg
1               5                   10                  15

Gly Gly Glu Pro
            20

<210> SEQ ID NO 58
<211> LENGTH: 20
<212> TYPE: PRT
<213> ORGANISM: Artificial Sequence
<220> FEATURE:
<223> OTHER INFORMATION: Synthetic construct

<400> SEQUENCE: 58

Lys Ser Arg Glu His Val Asn Asn Ser Ala Cys Pro Ser Lys Arg Ile
1               5                   10                  15

Thr Ala Ala Leu
            20

<210> SEQ ID NO 59
<211> LENGTH: 20
<212> TYPE: PRT
<213> ORGANISM: Artificial Sequence
<220> FEATURE:
<223> OTHER INFORMATION: Synthetic construct

<400> SEQUENCE: 59

Trp Leu Ser Glu Ala Gly Pro Val Val Thr Val Arg Ala Leu Arg Gly
1               5                   10                  15

Thr Gly Ser Trp
            20

<210> SEQ ID NO 60
<211> LENGTH: 20
<212> TYPE: PRT
<213> ORGANISM: Artificial Sequence
<220> FEATURE:
<223> OTHER INFORMATION: Synthetic construct

<400> SEQUENCE: 60

Thr Gly Gly Glu Thr Ser Gly Ile Lys Lys Ala Pro Tyr Ala Ser Thr
1               5                   10                  15

Thr Arg Asn Arg
            20

<210> SEQ ID NO 61
<211> LENGTH: 20
<212> TYPE: PRT
<213> ORGANISM: Artificial Sequence
```

<220> FEATURE:
<223> OTHER INFORMATION: Synthetic construct

<400> SEQUENCE: 61

Ser His His Gly Val Ala Gly Val Asp Leu Gly Gly Gly Ala Asp Phe
1               5                   10                  15

Lys Ser Ile Ala
            20

<210> SEQ ID NO 62
<211> LENGTH: 24
<212> TYPE: PRT
<213> ORGANISM: Artificial Sequence
<220> FEATURE:
<223> OTHER INFORMATION: Synthetic construct

<400> SEQUENCE: 62

Ser Asn Ser Pro Leu Gly Leu Lys Asp Glu Ala Thr Gln Arg Leu Val
1               5                   10                  15

Leu Glu Gln Ala Lys Trp Leu Ala
            20

<210> SEQ ID NO 63
<211> LENGTH: 20
<212> TYPE: PRT
<213> ORGANISM: Artificial Sequence
<220> FEATURE:
<223> OTHER INFORMATION: Synthetic construct

<400> SEQUENCE: 63

Gly Pro Glu Asp Thr Ser Arg Ala Pro Glu Asn Gln Gln Lys Thr Phe
1               5                   10                  15

His Arg Arg Trp
            20

<210> SEQ ID NO 64
<211> LENGTH: 22
<212> TYPE: PRT
<213> ORGANISM: Artificial Sequence
<220> FEATURE:
<223> OTHER INFORMATION: Synthetic construct

<400> SEQUENCE: 64

Ser Gly Glu Thr Gly Ser Asn Leu Val Gly His Glu Leu Asp Phe Arg
1               5                   10                  15

Pro Gly Ser Pro Ser Pro
            20

<210> SEQ ID NO 65
<211> LENGTH: 20
<212> TYPE: PRT
<213> ORGANISM: Artificial Sequence
<220> FEATURE:
<223> OTHER INFORMATION: Synthetic construct

<400> SEQUENCE: 65

Arg Tyr Ser Pro Ala Ala Thr Ala Glu Gly Arg Ser Val Ser Lys Glu
1               5                   10                  15

Leu Leu Arg Val
            20

<210> SEQ ID NO 66
<211> LENGTH: 20
<212> TYPE: PRT

<213> ORGANISM: Artificial Sequence
<220> FEATURE:
<223> OTHER INFORMATION: Synthetic construct

<400> SEQUENCE: 66

Gly Gln Glu Leu Gly Ala Trp Thr Arg Ser Lys Gly Pro Glu Val Gln
1               5                   10                  15

Thr Ser Val Leu
            20

<210> SEQ ID NO 67
<211> LENGTH: 20
<212> TYPE: PRT
<213> ORGANISM: Artificial Sequence
<220> FEATURE:
<223> OTHER INFORMATION: Synthetic construct

<400> SEQUENCE: 67

Ala Ser Thr Trp Arg Gly Thr Ser Ala Gly Gly Asn Arg Leu Glu Lys
1               5                   10                  15

Met Glu Val Thr
            20

<210> SEQ ID NO 68
<211> LENGTH: 20
<212> TYPE: PRT
<213> ORGANISM: Artificial Sequence
<220> FEATURE:
<223> OTHER INFORMATION: Synthetic construct

<400> SEQUENCE: 68

Leu Ser Gly Thr Pro Glu Arg Ser Gly Gln Ala Val Lys Val Lys Leu
1               5                   10                  15

Lys Ala Ile Pro
            20

<210> SEQ ID NO 69
<211> LENGTH: 20
<212> TYPE: PRT
<213> ORGANISM: Artificial Sequence
<220> FEATURE:
<223> OTHER INFORMATION: Synthetic construct

<400> SEQUENCE: 69

Gly Ala Trp Glu Ala Val Arg Asp Arg Ile Ala Glu Trp Gly Ser Trp
1               5                   10                  15

Gly Ile Pro Ser
            20

<210> SEQ ID NO 70
<211> LENGTH: 20
<212> TYPE: PRT
<213> ORGANISM: Artificial Sequence
<220> FEATURE:
<223> OTHER INFORMATION: Synthetic construct

<400> SEQUENCE: 70

Ala Met Asp Met Tyr Ser Ile Glu Asp Arg Tyr Phe Gly Gly Tyr Ala
1               5                   10                  15

Pro Glu Val Gly
            20

<210> SEQ ID NO 71
<211> LENGTH: 11

```
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (11)..(11)
<223> OTHER INFORMATION: PEG11-C-NH2

<400> SEQUENCE: 71

Tyr Ala Ala Trp Pro Ala Ser Gly Ala Trp Thr
1               5                   10

<210> SEQ ID NO 72
<211> LENGTH: 15
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (15)..(15)
<223> OTHER INFORMATION: PEG11-C-NH2
<220> FEATURE:
<221> NAME/KEY: MOD_RES
<222> LOCATION: (15)..(15)
<223> OTHER INFORMATION: ACETYLATION

<400> SEQUENCE: 72

Leu Gln Trp Arg Arg Asn Phe Gly Val Trp Ala Arg Tyr Arg Leu
1               5                   10                  15

<210> SEQ ID NO 73
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (10)..(10)
<223> OTHER INFORMATION: PEG11-YC-NH2

<400> SEQUENCE: 73

Arg Gly Asp Leu Ala Thr Leu Arg Gln Leu
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (10)..(10)
<223> OTHER INFORMATION: PEG11-YC-NH2

<400> SEQUENCE: 74

Arg Gly Asp Leu Ala Thr Leu Arg Gln Leu
```

<210> SEQ ID NO 75
<211> LENGTH: 15
<212> TYPE: PRT
<213> ORGANISM: Artificial Sequence
<220> FEATURE:
<223> OTHER INFORMATION: Synthtic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (15)..(15)
<223> OTHER INFORMATION: PEG11-C-NH2

<400> SEQUENCE: 75

Leu Gln Trp Arg Arg Asn Phe Gly Val Trp Ala Arg Tyr Arg Leu
1               5                   10                  15

<210> SEQ ID NO 76
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (10)..(10)
<223> OTHER INFORMATION: PEG11-C-NH2

<400> SEQUENCE: 76

Phe His Ala Val Pro Gln Ser Phe Tyr Thr
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (10)..(10)
<223> OTHER INFORMATION: PEG11-C-NH2

<400> SEQUENCE: 77

Phe His Ala Val Pro Gln Ser Phe Tyr Thr
1               5                   10

<210> SEQ ID NO 78
<211> LENGTH: 9
<212> TYPE: PRT
<213> ORGANISM: Artificial Sequence
<220> FEATURE:
<223> OTHER INFORMATION: Synthetic construct

<400> SEQUENCE: 78

Phe His Ala Val Pro Gln Ser Phe Tyr
1               5

```
<210> SEQ ID NO 79
<211> LENGTH: 9
<212> TYPE: PRT
<213> ORGANISM: Artificial Sequence
<220> FEATURE:
<223> OTHER INFORMATION: Synthetic construct

<400> SEQUENCE: 79

His Ala Val Pro Gln Ser Phe Tyr Thr
1               5

<210> SEQ ID NO 80
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION

<400> SEQUENCE: 80

Phe His Ala Val Pro Gln Ser Phe Tyr Thr
1               5                   10

<210> SEQ ID NO 81
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION

<400> SEQUENCE: 81

Leu Arg Gly Asp Leu Ala Thr Leu Arg Gln Leu
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION

<400> SEQUENCE: 82

Tyr Ala Ala Trp Pro Ala Ser Gly Ala Trp Thr
1               5                   10

<210> SEQ ID NO 83
<211> LENGTH: 20
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION

<400> SEQUENCE: 83

Leu Gln Trp Arg Arg Asp Asp Asn Val His Asn Phe Gly Val Trp Ala
1               5                   10                  15
```

```
Arg Tyr Arg Leu
            20

<210> SEQ ID NO 84
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION

<400> SEQUENCE: 84

Lys Gln Tyr Ala Thr Pro Arg Val Phe Trp Thr
1               5                   10
```

MOLECULAR GUIDE SYSTEM PEPTIDES AND USES THEREOF

CROSS REFERENCE TO RELATED PATENT APPLICATIONS

This application is a U.S. national phase application of International Application No. PCT/US2018/041403, which was filed on Jul. 10, 2018, and claims priority to U.S. Provisional Application No. 62/530,633, which was filed on Jul. 10, 2017. The content of these earlier filed applications is hereby incorporated by reference herein in its entirety.

INCORPORATION OF THE SEQUENCE LISTING

The present application contains a sequence listing that was submitted herewith in ASCII format via EFS-Web, containing the file name "37794_0002U2_SL" which is 24,576 bytes in size, created on Jan. 3, 2020, and is herein incorporated by reference in its entirety pursuant to 37 C.F.R. § 1.52(e)(5).

BACKGROUND

There is an overwhelming need for systematic cell-targeting systems that deliver therapeutic antibodies to a specific cell type and to specific locations within that cell.

The therapeutic monoclonal antibody (MAb) market has grown dramatically to over $70B within the past decade, and is anticipated to grow to $125B by 2020. There are currently 47 therapeutic MAbs in market that have FDA approval for a range of diseases. MAbs, however, are not cell permeable and as such they are limited to extracellular and cell surface therapeutic targets. This leaves a wealth of therapeutic targets within the cell, particularly protein-protein interactions, unavailable to MAb therapy. MAbs are otherwise uniquely powerful in their ability to modulate protein-protein interactions, so that their inability to penetrate cells and modulate intracellular protein-protein interactions constitutes a major unmet need in the treatment of life-threatening maladies such as infectious diseases, cancer, and other challenging and intractable diseases.

BRIEF SUMMARY

MAbs are uniquely powerful in their ability to modulate protein-protein interactions; their inability to penetrate cells and modulate intracellular protein-protein interactions constitutes a major unmet need in the treatment of life-threatening maladies. The ability to deliver therapeutic MAbs to a specific target cell, and to the right compartment within that cell, will have numerous societal health benefits. MGS-MAb combinations will create a new class of safe and efficacious intracellular acting drugs with the potential to treat heretofore "undruggable" targets. Disclosed herein are composition and methods utilizing molecular guidance system (MGS) peptides that provide new therapeutic strategies for the treatment of emerging infectious diseases and bioterrorism, novel therapies for cancer, diabetes, neurological and neurodegenerative diseases and even genetically inherited diseases.

Disclosed are compositions comprising an antibody conjugated to one or more molecular guidance system (MGS) peptides.

Disclosed are compositions comprising an antibody conjugated to one or more MGS peptides, wherein the antibody targets an intracellular target.

Disclosed are compositions comprising an antibody conjugated to one or more MGS peptides, wherein the antibody is a monoclonal antibody. In some aspects, the monoclonal antibody is an anti-Ras monoclonal antibody.

Disclosed are compositions comprising an antibody conjugated to one or more MGS peptides, wherein the one or more MGS peptides comprises the sequence of EHPWFNMWSWATQVQE (SEQ ID NO:38), YPGSPTQYPSSMHEYHSSSE (SEQ ID NO:39), AHTIDDEWASYHMQQWNSPP (SEQ ID NO:40), FEEFYSRQSNTIPYPQQYKG (SEQ ID NO:41), THGNKHQSWTYPSEINHKNY (SEQ ID NO:19), NLADTWTQTQQHDFHVLRGTR (SEQ ID NO:20), GYSWWQPNWPSSTWDT (SEQ ID NO:21) or a combination thereof. In some aspects, the one or more MGS peptides comprises the sequence of EHPWFNMWSWATQVQE (SEQ ID NO:38). Disclosed are compositions comprising an antibody conjugated to one or more MGS peptides, wherein the one or more MGS peptides comprises the sequence of SEQ ID NO: 1, 2, 3, 34, 35, 36, 37, 38, 39, 40, 41, 41, 42, 43, 44, 45, 46, 47, 48, 49, 50, 51, 52, 5, 54, 55, 56, 57, 58, 59, 60, 61, 62, 63, 64, 65, 66, 67, 68, 69, 70, 71, 72, 73, 74, 75, 76, or 77 or a combination thereof Disclosed are compositions comprising an antibody conjugated to one or more MGS peptides, wherein the one or more MGS peptides localize to one or more intracellular targets.

Disclosed are compositions comprising an antibody conjugated to one or more MGS peptides, wherein the one or more MGS peptides localize to one or more intracellular targets, wherein the intracellular target is the lysosome, golgi apparatus, endoplasmic reticulum, cytoplasm, or nucleus.

Disclosed are compositions comprising an antibody conjugated to one or more MGS peptides, wherein the antibody is conjugated to the one or more MGS peptides via a linker.

Disclosed are compositions comprising an antibody conjugated to one or more MGS peptides, wherein the antibody conjugated to the one or more MGS peptides is a fusion protein.

Disclosed are methods of targeting an intracellular target comprising administering an antibody conjugated to one or more MGS peptides, wherein the antibody targets an intracellular target. In some aspects, the intracellular target is the lysosome, Golgi apparatus, endoplasmic reticulum, cytoplasm, or nucleus.

Disclosed are methods of treating a subject in need thereof comprising administering to the subject in need thereof an effective amount of an antibody conjugated to one or more MGS peptides, wherein the antibody targets an intracellular target involved in the disease process. In some aspects, the subject in need thereof has an infectious disease, cancer, diabetes, a neurological or neurodegenerative disease, a genetically-inherited disease, or been exposed to a bioterrorism agent.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 18 shows a table of MGS sequences. The sequences in the selected sequence column has SEQ ID NOs:34-70 listed from top to bottom, respectively. The optimized sequence column has SEQ ID NOs:71-77 listed from top to bottom, respectively.

FIG. 25 shows determined effective dose, stoichiometry, and rate of uptake for 4 MGSs on 4 NSCLC cell lines.

DETAILED DESCRIPTION

Figure 1:
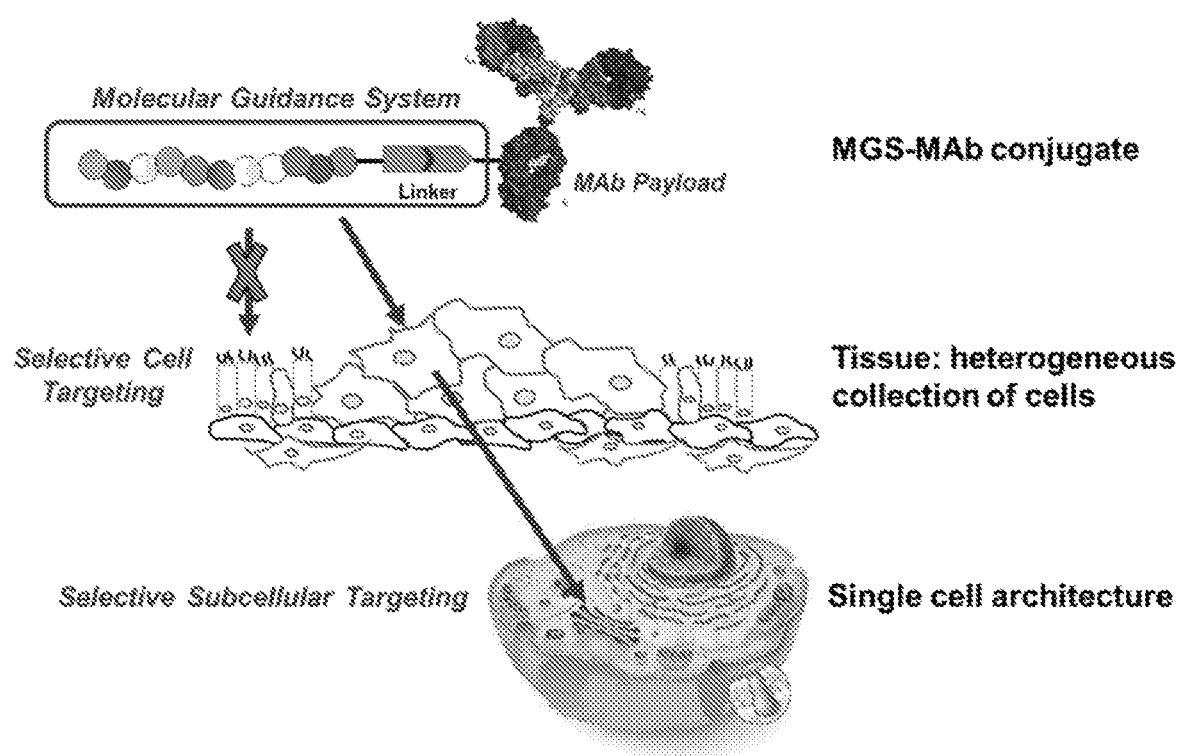
FIG. 1 is a schematic diagram of the Molecular Guidance Systems. The molecular targeting peptide will be identified by the FOX-Three technology. The peptide will deliver the cargo specifically to the target cell while avoiding uptake in other cells. Upon internalization, the peptide will direct the cargo to the desired location within the cell. The linker can be stable or designed to release the cargo upon reaching its target. The system is modular so that the cargo can be virtually any bioactive compound.

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a conjugate is disclosed and discussed and a number of modifications that can be made to a number of molecules including the MGS peptide are discussed, each and every combination and permutation of the conjugates and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a MGS peptide" includes a plurality of such MGS peptides, reference to "the MGS peptide" is a reference to one or more MGS peptides and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

As used herein, the term "subject" refers to any organism to which a composition of disclosed herein can be administered, e.g., for experimental, diagnostic, and/or therapeutic purposes. Typical subjects include animals (e.g., mammals such as non-human primates, and humans; avians; domestic household or farm animals such as cats, dogs, sheep, goats, cattle, horses and pigs; laboratory animals such as mice, rats and guinea pigs; rabbits; fish; reptiles; zoo and wild animals) and/or plants. Typically, "subjects" are animals, including mammals such as humans and primates; and the like.

As used herein, the term "patient" refers to a subject afflicted with a disease or disorder. The term "patient" includes human and veterinary subjects. In some aspects of the disclosed methods, the "patient" has been diagnosed with a need for treatment for an autoimmune disorder, such as, for example, prior to the administering step.

As used herein, the term "amino acid sequence" refers to a list of abbreviations, letters, characters or words representing amino acid residues. The amino acid abbreviations used herein are conventional one letter codes for the amino acids and are expressed as follows: A, alanine; C, cysteine; D aspartic acid; E, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine.

"Polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules.

In addition, as used herein, the term "polypeptide" refers to amino acids joined to each other by peptide bonds or modified peptide bonds, e.g., peptide isosteres, etc. and may contain modified amino acids other than the 20 gene-encoded amino acids. The polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide. Also, a given polypeptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, myristoylation, oxidation, pergylation, proteolytic processing, phosphorylation, prenylation, racemization, selenoylation, sulfation, and transfer-RNA mediated addition of amino acids to protein such as arginylation. (See Proteins—*Structure and Molecular Properties* 2nd Ed., T. E. Creighton, W. H. Freeman and Company, New York (1993); *Posttranslational Covalent Modification of Proteins*, B. C. Johnson, Ed., Academic Press, New York, pp. 1-12 (1983)).

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof As used herein, "sample" is meant to mean an animal; a tissue or organ from an animal; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

As used herein, "modulate" is meant to mean to alter, by increasing or decreasing.

As used herein, "effective amount" of a compound is meant to mean a sufficient amount of the compound to provide the desired effect. The exact amount required will vary from subject to subject, depending on the species, age, and general condition of the subject, the severity of disease (or underlying genetic defect) that is being treated, the particular compound used, its mode of administration, and the like. Thus, it is not possible to specify an exact "effective amount." However, an appropriate "effective amount" may be determined by one of ordinary skill in the art using only routine experimentation.

As used herein, "isolated polypeptide" or "purified polypeptide" is meant to mean a polypeptide (or a fragment thereof) that is substantially free from the materials with which the polypeptide is normally associated in nature. The polypeptides of the invention, or fragments thereof, can be obtained, for example, by extraction from a natural source (for example, a mammalian cell), by expression of a recombinant nucleic acid encoding the polypeptide (for example, in a cell or in a cell-free translation system), or by chemically synthesizing the polypeptide. In addition, polypeptide fragments may be obtained by any of these methods, or by cleaving full length proteins and/or polypeptides.

As used herein, "isolated nucleic acid" or "purified nucleic acid" is meant to mean DNA that is free of the genes that, in the naturally-occurring genome of the organism from which the DNA of the invention is derived, flank the gene. The term therefore includes, for example, a recombinant DNA which is incorporated into a vector, such as an autonomously replicating plasmid or virus; or incorporated into the genomic DNA of a prokaryote or eukaryote (e.g., a transgene); or which exists as a separate molecule (for example, a cDNA or a genomic or cDNA fragment produced by PCR, restriction endonuclease digestion, or chemical or in vitro synthesis). It also includes a recombinant DNA which is part of a hybrid gene encoding additional polypeptide sequence. The term "isolated nucleic acid" also refers to RNA, e.g., an mRNA molecule that is encoded by an isolated DNA molecule, or that is chemically synthesized, or that is separated or substantially free from at least some cellular components, for example, other types of RNA molecules or polypeptide molecules.

As used herein, "prevent" is meant to mean minimize the chance that a subject who has an increased susceptibility for developing cancer will develop cancer.

As used herein, "specifically binds" is meant that an antibody recognizes and physically interacts with its cognate antigen or target (for example, the disclosed synthetic MGS sequences) and does not significantly recognize and interact with other antigens or targets; such an antibody may be a polyclonal antibody or a monoclonal antibody, which are generated by techniques that are well known in the art.

As used herein, "probe," "primer," or oligonucleotide is meant to mean a single-stranded DNA or RNA molecule of defined sequence that can base-pair to a second DNA or RNA molecule that contains a complementary sequence (the "target"). The stability of the resulting hybrid depends upon the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes or primers specific for nucleic acids capable of encoding the disclosed MGS sequences (for example, genes and/or mRNAs) have at least 80%-90% sequence complementarity, preferably at least 91%-95% sequence complementarity, more preferably at least 96%-99% sequence complementarity, and most preferably 100% sequence complementarity to the region of the nucleic acid capable of encoding the disclosed MGS sequences to which they hybridize. Probes, primers, and oligonucleotides may be detectably-labeled, either radioactively, or non-radioactively, by methods well-known to those skilled in the art. Probes, primers, and oligonucleotides are used for methods involving nucleic acid hybridization, such as: nucleic acid sequencing, reverse transcription and/or nucleic acid amplification by the polymerase chain reaction, single stranded conformational polymorphism (SSCP) analysis, restriction fragment polymorphism (RFLP) analysis, Southern hybridization, Northern hybridization, in situ hybridization, electrophoretic mobility shift assay (EMSA).

As used herein, "specifically hybridizes" is meant to mean that a probe, primer, or oligonucleotide recognizes and physically interacts (that is, base-pairs) with a substantially complementary nucleic acid (for example, a nucleic acid capable of encoding the disclosed MGS sequence) under high stringency conditions, and does not substantially base pair with other nucleic acids.

As used herein, "high stringency conditions" is meant to mean conditions that allow hybridization comparable with that resulting from the use of a DNA probe of at least 40 nucleotides in length, in a buffer containing 0.5 M $NaHPO_4$, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well-known by those skilled in the art of molecular biology. (See, for example, F. Ausubel et al., Current Protocols in Molecular Biology, John Wiley & Sons, New York, NY, 1998).

As used herein, the term "therapeutically effective amount" means an amount of a therapeutic, prophylactic, and/or diagnostic agent (e.g., MGS peptide conjugated to an antibody) that is sufficient, when administered to a subject suffering from or susceptible to a disease, disorder, and/or condition, to treat, alleviate, ameliorate, relieve, alleviate symptoms of, prevent, delay onset of, inhibit progression of, reduce severity of, and/or reduce incidence of the disease, disorder, and/or condition.

As used herein, the term "treating" refers to partially or completely alleviating, ameliorating, relieving, delaying onset of, inhibiting progression of, reducing severity of, and/or reducing incidence of one or more symptoms or features of a particular disease, disorder, and/or condition. For example, "treating" a microbial infection may refer to inhibiting survival, growth, and/or spread of the microbe. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. In some embodiments, treatment comprises delivery of one or more of the disclosed compositions to a subject.

The term "antibody", as used herein, also includes full length antibodies and antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide). Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

The antibodies described herein can be recombinant, chimeric, or humanized antibodies. The term "chimeric antibody" refers to an antibody that contains one or more regions from one antibody and one or more regions from one or more other antibodies. A "humanized antibody" has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject.

Ranges may be expressed herein as from "about" one particular value, and/or to "about" another particular value. When such a range is expressed, also specifically contemplated and considered disclosed is the range¬from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

B. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Disclosed are compositions comprising an antibody conjugated to one or more MGS peptides. In some aspects, the antibody targets an intracellular target.

Disclosed are compositions comprising an antibody conjugated to one or more MGS peptides, wherein the antibody is a monoclonal antibody. In some aspects, the monoclonal antibody can be an anti-Ras monoclonal antibody.

MGS peptides. Disclosed herein are MGS or targeting peptides. These peptides can bind selectively to cells. Examples of MGS peptides that can be used or modified in the disclosed compositions can include, but are not limited to, one or more of the MGS peptides disclosed in McGuire et al., Sci Rep. 2014 Mar. 27; 4:4480. Examples of MGS peptides that can also be used in the disclosed compositions and methods, include, but are not limited to the MGS sequences shown in Table 1 and FIGS. 9 and 10.

TABLE 1

Peptide sequences.

| Peptide Name | Peptide Sequence | SEQ ID NO: |
|---|---|---|
| HCC15.2 | FHAVPQSFYTAP | 1 |
|  | FHAVPQSFYTA | 2 |
|  | FHAVPQSFYT | 3 |
|  | FHAVPQSFY | 78 |
|  | HAVPQSFYT | 79 |
|  | CH3CO— FHAVPQSFYT | 80 |
| H1299.1 | VSQTMRQTAVPLLWFWTGSL | 4 |
| H1299.2 | YAAWPASGAWTGTAPCSAGT | 5 |
|  | YAAWPASGAWT | 6 |
|  | CH3CO-YAAWPASGAWT | 82 |
| H2009.1 | RGDLATLRQLAQEDGVVGVR | 7 |
|  | D-Leu-RGDLATLRQL | 8 |
|  | CH3CO— D-Leu-RGDLATLRQL | 81 |
| H460.1 | EAMNSAEQSAAVVQWEKRRI | 9 |
| HCC15.1 | ATEPRKQYATPRVFWTDAPG | 10 |
| A549.1 | MTVCNASQRQAHAQATAVSL | 11 |
| HCC95.1 | MRGQTGKLPTEHFTDTGVAF | 12 |
| H1155.1 | MTGKAAAPHQEDRHANGLEQ | 13 |
| H661.1 | TNSCRGDWLCDAVPEKARV | 14 |
|  | EHPWFNMWSWATQVQE | 15 |
| H2009.2 | YPGSPTQYPSSMHEYHSSSE | 16 |
| H2009.3 | AHTIDDEWASYHMQQWNSPP | 17 |
|  | FEEFYSRQSNTIPYPQQYKG | 18 |
|  | THGNKHQSWTYPSEINHKNY | 19 |
|  | NLADTWTQTQQHDFHVLRGTR | 20 |
|  | GYSWWQPNWPSSTWDT | 21 |
| H1299.4 | EHPWFNMWSWATQVQEKKK | 22 |
| H2009.4 | NLADTWTQTQQHDFHVLRGT | 23 |
| H1993.1 | SVEYWGERMYYDVMESLGFS | 24 |
| H1993.2 | FAAKRAEWWDPGQLWDAVWN | 25 |
| H1993.3 | QEALEEWFWKMMPWSGPSGQ | 26 |
| H1993.4 | TWTDFGQWPWPFGAEGTRAF | 27 |
| H1993.5 | MDGATWWTQLDPLLVWEGET | 28 |
| H1993.5 | SADWFQGPAEWLLEGWMGPL | 29 |
| H1299.3 | LQWRRDDNVHNFGVWARYRL | 30 |
|  | LQWRRNFGVWARYRL | 31 |
| HCC15.1 | ATEPRKQYATPRVFWTDAPG | 32 |
|  | KQYATPRVFWT | 33 |
|  | CH3CO— KQYATPRVFWT | 84 |

TABLE 1-continued

Peptide sequences.

| Peptide Name | Peptide Sequence | SEQ ID NO: |
|---|---|---|
| MGS_H1299.1 | VSQTMRQTAVPLLWFWTGSL | 34 |
| MGS_1299.2 | YAAWPASGAWTGTAPCSAGT | 35 |
| MGS_1299.3 | LQWRRDDNVHNFGVWARYRL | 36 |
| | CH3CO— LQWRRDDNVHNFGVWARYRL | 83 |
| MGS_H2009.1 | RGDLATLRQLAQEDGVVGVR | 37 |
| MGS_H2009.2 | EHPWFNMWSWATQVQE | 38 |
| MGS_H2009.3 | YPGSPTQYPSSMHEYHSSSE | 39 |
| MGS_H2009.4 | AHTIDDEWASYHMQQWNSPP | 40 |
| MGS_H2009.5 | FEEFYSRQSNTIPYPQQYKG | 41 |
| MGS_HCC15.1 | ATEPRKQYATPRVFWTDAPG | 42 |
| MGS_HCC15.2 | FHAVPQSFYTAP | 43 |
| MGS_H460.1 | EAMNSAEQSAAVVQWEKRRI | 44 |
| MGS_A549.1 | MTVCNASQRQAHAQATAVSL | 45 |
| MGS_MCF7.1 | LTVHGRGPEYNPSWNRRAFP | 46 |
| MGS_H1993.1 | SVEYWGERMYYDVMESLGFS | 47 |
| MGS_H1993.2 | FAAKRAEWWDPGQLWDAVWN | 48 |
| MGS_H1993.3 | QEALEEWFWKMMPWSGPSGQ | 49 |
| MGS_H1993.4 | TWTDFGQWPWPFGAEGTRAF | 50 |
| MGS_H1993.5 | MDGATWWTQLDPLLVWEGET | 51 |
| MGS_H1993.6 | SADWFQGPAEWLLEGWMGPL | 52 |
| MGS_HCC95.1 | MRGQTGKLPTEHFTDTGVAF | 53 |
| MGS_H1155.1 | MTGKAAAPHQEDRHANGLEQ | 54 |
| MGS_H1155.2 | MEKLPLSKTGRTVSEGVSPP | 55 |
| MGSH666.1 | TNSCRGDWLCDAVPEKARV | 56 |
| MGS_A20.1 | SAKTAVSQRVWLPSHRGGEP | 57 |
| MGS_A20.2 | KSREHVNNSACPSKRITAAL | 58 |
| MGS_PCM.1 | WLSEAGPVVTVRALRGTGSW | 59 |
| MGS_C2C12.1 | TGGETSGIKKAPYASTTRNR | 60 |
| MGS_C2C12.2 | SHHGVAGVDLGGGADFKSIA | 61 |
| MGS_C2C12.3 | SNSPLGLKDEATQRLVLEQAKWLA | 62 |
| MGS_XS52.1 | GPEDTSRAPENQQKTFHRRW | 63 |
| MGS_XS52.2 | SGETGSNLVGHELDFRPGSPSP | 64 |
| MGS_XS106.1 | RYSPAATAEGRSVSKELLRV | 65 |
| MGS_717US.1 | GQELGAWTRSKGPEVQTSVL | 66 |
| MGS_717S.1 | ASTWRGTSAGGNRLEKMEVT | 67 |
| MGS_RIP.1 | LSGTPERSGQAVKVKLKAIP | 68 |
| MGS_RIP.2 | GAWEAVRDRIAEWGSWGIPS | 69 |
| MGS_MArg.1_Bacterial | AMDMYSIEDRYFGGYAPEVG | 70 |

TABLE 1-continued

Peptide sequences.

| Peptide Name | Peptide Sequence | SEQ ID NO: |
|---|---|---|
| MGS_1299.2 V4 | $CH_3CO$—YAAWPASGAWT—$PEG_{11}$—C—$NH_2$ | 71 |
| MGS_1299.3 V2 | $CH_3CO$—LQWRRNFGVWARYRL—$PEG_{11}$—C—$NH_2$ | 72 |
| MGS_2009.1 V4 | $CH_3CO$—RGDLATLRQL—$PEG_{11}$—YC—$NH_2$ | 73 |
| MGS_H2009.1 V5 | $CH_3CO$—d(Leu)—RGDLATLRQL—$PEG_{11}$—YC—$NH_2$ | 74 |
| MGS_HC C15.1 V4 | $CH_3CO$—LQWRRNFGVWARYRL—$PEG_{11}$—C—$NH_2$ | 75 |
| MGS_HCC15.2 V8 | $CH_3CO$—FHAVPQSFYT—$PEG_{11}$—C—$NH_2$ | 76 |
| MGS_HCC15.2 V9 | $CH_3CO$—FHAVPQSFYT—$PEG_{11}$—C—$NH_2$ | 77 |

SEQ ID NOs:71-77 are optimized MGS peptides. Optimized peptides were obtained by applying modifications to the individual parental peptide sequence identified by the FOX-3 platform technology. These modifications are used to identify the essential amino acids within the parental sequence that are required for cell-specific binding and internalization. These modifications are obtained by a combination of alanine scanning and truncations of the amino-terminal region and c-terminal region of the parental peptide. PEG11 provides protection of the C-terminus of the MGS peptide, provides a spacer between the peptide and the cargo molecule attached through the cysteine at the C-terminus, and enhances solubility of the MGS-peptide. Modification at the amino-terminus by acetylation (CH3CO—) and/or d-amino acids, such as d(Leu) protect against degradation by peptidases in blood. There is not a uniform length of optimized peptide that can be applied to all MGS peptides and all changes need to be tested to confirm the effect on peptide uptake and stability. In peptide 73, the YC is used to allow us to monitor peptide synthesis and concentration by the absorbance of light at 280 nm. Without the addition of tyrosine (Y), this peptide would be significantly more difficult to monitor.

Disclosed are modified peptides comprising the sequence of $CH_3CO$-YAAWPASGAWT-$PEG_{11}$-C—$NH_2$ (SEQ ID NO:71), $CH_3CO$-LQWRRNFGVWARYRL-$PEG_{11}$-C—$NH_2$ (SEQ ID NO:72), $CH_3CO$-d(Leu)-RGDLATLRQL-$PEG_{11}$-YC—$NH_2$ (SEQ ID NO:74), $CH_3CO$-LQWRRNFGVWARYRL-$PEG_{11}$-C—$NH_2$. (SEQ ID NO:75), $CH_3CO$-FHAVPQSFYT-$PEG_{11}$-C—$NH_2$ (SEQ ID NO:76), or $CH_3CO$-FHAVPQSFYT-$PEG_{11}$-C—$NH_2$ (SEQ ID NO:77).

Disclosed are any of the MGS peptides described in table 1.

In an aspect, the compositions comprise one or more of the MGS peptides and an antibody. In an aspect, the compositions comprise one or more of the MGS peptides disclosed herein and an antibody. In an aspect, the membrane-permeable conjugates for transport across a lipid membrane can comprise one or more MGS peptides and an antibody.

In an aspect, the one or more MGS peptides can be any of the MGS peptides disclosed herein. In an aspect, the one or more MGS peptides comprise SEQ ID NO: 1, 2, 3, 34, 35, 36, 37, 38, 39, 40, 41, 41, 42, 43, 44, 45, 46, 47, 48, 49, 50, 51, 52, 5, 54, 55, 56, 57, 58, 59, 60, 61, 62, 63, 64, 65, 66, 67, 68, 69, 70, 71, 72, 73, 74, 75, 76, 77, 78, 79, 81, 81, 82, 83, 84 or a combination thereof.

In an aspect, the one or more MGS peptides comprise SEQ ID NOs: 1, 2, 3, 34, 35, 36, 37, 38, 39, 40, 41, 41, 42, 43, 44, 45, 46, 47, 48, 49, 50, 51, 52, 5, 54, 55, 56, 57, 58, 59, 60, 61, 62, 63, 64, 65, 66, 67, 68, 69, 70, 71, 72, 73, 74, 75, 76, 77, 78, 79, 81, 81, 82, 83, or 84. In an aspect, the one or more MGS peptides can be SEQ ID NO: 3. In an aspect, the compositions can comprise one or more MGS peptides, for example, in some aspects, the composition can comprise, one, two, three, four or five MGS peptides. In an aspect, the one or more MGS peptides can form a tetrameric scaffold protein. In an aspect, the one or more MGS peptides disclosed herein can be truncated.

In an aspect, the one or more MGS peptides can be modified. In an aspect, the one or more MGS peptides can acetylated on the N-terminus. In an aspect, the one or more MGS peptides can be chemically conjugated to an antibody. In an aspect, the chemical conjugate can be polyethylene glycol (PEG). In an aspect, the number of PEG units can be 1, 2, 3, 4, 5, 6, 7, 8, 9, 10, 11, or more. In aspect, the number of PEG units can be of sufficient length to separate the one or more MGS peptides from the antibody to prevent any steric interference between the one or more MGS peptides and the antibody. For example, disclosed herein are compositions comprising a chemical conjugate, wherein the chemical conjugate is PEG and the PEG comprises eleven PEG units. In an aspect, the one or more MGS peptides comprise SEQ ID NO: 3, wherein SEQ ID NO: 3 can be acetylated on the N-terminus and can be chemically conjugated to PEG; and the antibody, wherein the antibody can be covalently attached to PEG.

Disclosed are compositions comprising an antibody conjugated to one or more MGS peptides, wherein the one or more MGS peptides comprises the sequence of EHPWFNMWSWATQVQE (SEQ ID NO:38), YPGSPTQYPSSMHEYHSSSE (SEQ ID NO:39), AHTIDDEWASYHMQQWNSPP (SEQ ID NO:40), FEEFYSRQSNTIPYPQQYKG (SEQ ID NO:41), THGNKHQSWTYPSEINHKNY (SEQ ID NO:19), NLADTWTQTQQHDFHVLRGTR (SEQ ID NO:20), GYSWWQPNWPSSTWDT (SEQ ID NO:21) or a combination thereof. In some aspects, the one or more MGS peptides comprises the sequence of EHPWFNMWSWATQVQE (SEQ ID NO:38).

In some aspects of the disclosed compositions, the one or more MGS peptides localize to one or more intracellular targets. For example, the intracellular target can be, but is not limited to, the lysosome, golgi apparatus, endoplasmic reticulum, cytoplasm, or nucleus. Any subcellular compartment can be targeted.

The antibody and the one or more MGS peptides can be conjugated in any of the ways proteins are commonly conjugated or linked. In some aspects, the antibody can be conjugated to the one or more MGS peptides via a linker. For example, in some instances the linker can be a peptide linker or a nucleic acid linker. In some aspects the linker can be a cleavable linker. In some aspects, the antibody conjugated to the one or more MGS peptides is a fusion protein. In other words, the antibody conjugated to the one or more MGS peptides can be produced as one long protein comprising several different peptides, instead of being produced as separate peptides and then later conjugated or linked together. In some aspects, an MGS peptide can be conjugated to an antibody using any known conjugation methods, including but not limited to, SiteClick chemistry.

In some aspects of the disclosed compositions, the antibody can further comprise a label. For example, the compositions disclosed herein can include detectable labels. Such detectable labels can include, but are not limited to, a tag sequence designed for detection (e.g., purification or localization) of an expressed polypeptide or sequence. Tag sequences include, for example, green fluorescent protein, glutathione S-transferase, polyhistidine, c-myc, hemagglutinin, or Flag™ tag, and can be fused with an encoded nucleic acid. Such detectable labels can include, but are not limited to, a fluorescent agent, an enzymatic label, or a radioisotope.

In some aspects, the disclosed compositions can be pharmaceutical compositions. For example, in some aspects, disclosed are pharmaceutical compositions comprising a composition comprising an antibody conjugated to one or more MGS peptides and a pharmaceutically acceptable carrier. By "pharmaceutically acceptable" is meant a material or carrier that would be selected to minimize any degradation of the active ingredient and to minimize any adverse side effects in the subject, as would be well known to one of skill in the art. Examples of carriers include dimyristoylphosphatidyl (DMPC), phosphate buffered saline or a multivesicular liposome. For example, PG:PC:Cholesterol:peptide or PC:peptide can be used as carriers in this invention. Other suitable pharmaceutically acceptable carriers and their formulations are described in Remington: The Science and Practice of Pharmacy (19th ed.) ed. A. R. Gennaro, Mack Publishing Company, Easton, PA 1995. Typically, an appropriate amount of pharmaceutically-acceptable salt is used in the formulation to render the formulation isotonic. Other examples of the pharmaceutically-acceptable carrier include, but are not limited to, saline, Ringer's solution and dextrose solution. The pH of the solution can be from about 5 to about 8, or from about 7 to about 7.5. Further carriers include sustained release preparations such as semi-permeable matrices of solid hydrophobic polymers containing the composition, which matrices are in the form of shaped articles, e.g., films, stents (which are implanted in vessels during an angioplasty procedure), liposomes or microparticles. It will be apparent to those persons skilled in the art that certain carriers may be more preferable depending upon, for instance, the route of administration and concentration of composition being administered. These most typically would be standard carriers for administration of drugs to humans, including solutions such as sterile water, saline, and buffered solutions at physiological pH.

Pharmaceutical compositions can also include carriers, thickeners, diluents, buffers, preservatives and the like, as long as the intended activity of the polypeptide, peptide, or conjugate of the invention is not compromised. Pharmaceutical compositions may also include one or more active ingredients (in addition to the composition of the invention) such as antimicrobial agents, anti-inflammatory agents, anesthetics, and the like.

The pharmaceutical compositions as disclosed herein can be prepared for oral or parenteral administration. Pharmaceutical compositions prepared for parenteral administration include those prepared for intravenous (or intra-arterial), intramuscular, subcutaneous, intraperitoneal, transmucosal (e.g., intranasal, intravaginal, or rectal), or transdermal (e.g., topical) administration. Aerosol inhalation can also be used to deliver the fusion proteins. Thus, compositions can be prepared for parenteral administration that includes fusion proteins dissolved or suspended in an acceptable carrier, including but not limited to an aqueous carrier, such as water, buffered water, saline, buffered saline (e.g., PBS), and the like. One or more of the excipients included can help approximate physiological conditions, such as pH adjusting and buffering agents, tonicity adjusting agents, wetting agents, detergents, and the like. Where the compositions include a solid component (as they may for oral administration), one or more of the excipients can act as a binder or filler (e.g., for the formulation of a tablet, a capsule, and the like). Where the compositions are formulated for application to the skin or to a mucosal surface, one or more of the excipients can be a solvent or emulsifier for the formulation of a cream, an ointment, and the like.

The pharmaceutical compositions can be sterile and sterilized by conventional sterilization techniques or sterile filtered. Aqueous solutions can be packaged for use as is, or lyophilized, the lyophilized preparation, which is encompassed by the present disclosure, can be combined with a sterile aqueous carrier prior to administration. The pH of the pharmaceutical compositions typically will be between 3 and 11 (e.g., between about 5 and 9) or between 6 and 8 (e.g., between about 7 and 8). The resulting compositions in solid form can be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

C. Methods

Disclosed are methods of targeting an intracellular target comprising administering a therapeutically effective amount of one or more of the disclosed compositions.

Disclosed are methods of targeting an intracellular target comprising administering an antibody conjugated to one or more MGS peptides, wherein the antibody targets an intracellular target. In some aspects, the intracellular target can be the lysosome, golgi apparatus, endoplasmic reticulum, cytoplasm, or nucleus. Any subcellular compartment can be targeted.

In an aspect, skilled person can determine an efficacious dose, an efficacious schedule, or an efficacious route of administration for a disclosed composition or a disclosed fusion protein or a disclosed fusion protein so as to induce target an intracellular target such that the intracellular target can be inactivated.

Also disclosed are methods of treating a subject in need thereof comprising administering to the subject in need thereof an effective amount of an antibody conjugated to one or more MGS peptides, wherein the antibody targets an intracellular target involved in the disease process.

In an aspect of any of the disclosed methods herein, the composition, conjugate or fusion protein described herein can be combined with one or more additional therapies. In an aspect, the composition, conjugate or fusion protein can be administered alone or in combination with other biologically active agents into compositions suitable for administration to a subject. In an aspect, methods directed to treating subjects with cancer or at risk for developing cancer, the composition, conjugate or fusion protein disclosed herein can be combined with, for example, therapeutically effective amount of radiation therapy, immunotherapy or chemotherapy or a combination thereof. The combined therapy can be administered as a co-formulation, or separately. When administered separately, the combined therapy can be administered simultaneously or sequentially. The formulations can be made using methods routine in the art.

The pharmaceutical compositions described above can be formulated to include a therapeutically effective amount of a composition, conjugate or fusion protein as disclosed herein. Therapeutic administration encompasses prophylactic applications. Based on genetic testing and other prognostic methods, a physician in consultation with their patient can choose a prophylactic administration where the patient has a clinically determined predisposition or increased susceptibility (in some cases, a greatly increased susceptibility) to one or more autoimmune diseases or where the patient has a clinically determined predisposition or increased susceptibility (in some cases, a greatly increased susceptibility) to cancer.

The pharmaceutical compositions described herein can be administered to the subject (e.g., a human subject or human patient) in an amount sufficient to delay, reduce, or preferably prevent the onset of clinical disease. Accordingly, in some aspects, the subject is a human subject. In therapeutic applications, compositions are administered to a subject (e.g., a human subject) already with or diagnosed with an autoimmune disease in an amount sufficient to at least partially improve a sign or symptom or to inhibit the progression of (and preferably arrest) the symptoms of the condition, its complications, and consequences. An amount adequate to accomplish this is defined as a "therapeutically effective amount." A therapeutically effective amount of a pharmaceutical composition can be an amount that achieves a cure, but that outcome is only one among several that can be achieved. As noted, a therapeutically effective amount includes amounts that provide a treatment in which the onset or progression of the cancer is delayed, hindered, or prevented, or the autoimmune disease or a symptom of the autoimmune disease is ameliorated. One or more of the symptoms can be less severe. Recovery can be accelerated in an individual who has been treated.

The total effective amount of the conjugates or fusion proteins in the pharmaceutical compositions disclosed herein can be administered to a mammal as a single dose, either as a bolus or by infusion over a relatively short period of time, or can be administered using a fractionated treatment protocol in which multiple doses are administered over a more prolonged period of time (e.g., a dose every 4-6, 8-12, 14-16, or 18-24 hours, or every 2-4 days, 1-2 weeks, or once a month). Alternatively, continuous intravenous infusions sufficient to maintain therapeutically effective concentrations in the blood are also within the scope of the present disclosure.

The therapeutically effective amount of the antibody present within the compositions described herein and used in the methods as disclosed herein applied to mammals (e.g., humans) can be determined by one of ordinary skill in the art with consideration of individual differences in age, weight, and other general conditions (as mentioned above). Because the compositions, conjugates and fusion proteins of the present disclosure can be stable in serum and the bloodstream and in some cases more specific, the dosage of the compositions, conjugates and fusion proteins including any individual component can be lower (or higher) than an effective dose of any of the individual components when unbound. Accordingly, in some aspects, the antibody administered can have an increased efficacy or reduced side effects when administered as part of a conjugate or fusion protein as compared to when the antibody is administered alone or not as part of a conjugate or fusion protein.

In some aspects, the subject in need thereof has an infectious disease, cancer, diabetes, a neurological or neurodegenerative disease, a genetically-inherited disease, a lysosomal disease, a mitochondrial disease, or been exposed to a bioterrorism agent.

D. Vectors

Disclosed are vectors comprising the nucleic acid sequence that encodes for one or more of the disclosed compositions. In some aspects, the vector comprises only a nucleic acid sequence capable of encoding one or more of the disclosed MGS peptides.

E. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits comprising one or more of the disclosed compositions.

In some aspects the kits comprise a MGS peptide and a monoclonal antibody and instructions for conjugation.

In some aspects the kits comprise a cell line comprising a nucleic acid sequence that encodes one or more of the MGS peptides.

EXAMPLES

A. Example 1

Until recently, no systematic approaches to target intracellular/subcellular components have been reported. The propriety FOX-Three technology is a platform for the systematic discovery of MGSs capable of delivering a MAb to cellular and subcellular targets. The FOX-Three platform identifies MGSs with three key attributes: the ability to home in on a desired cell type, the ability to trigger cellular uptake, and the ability to deliver a payload to a discrete location within the targeted cell. A broad overview of how the MGS is shown in FIG. 1.

Figure 2:
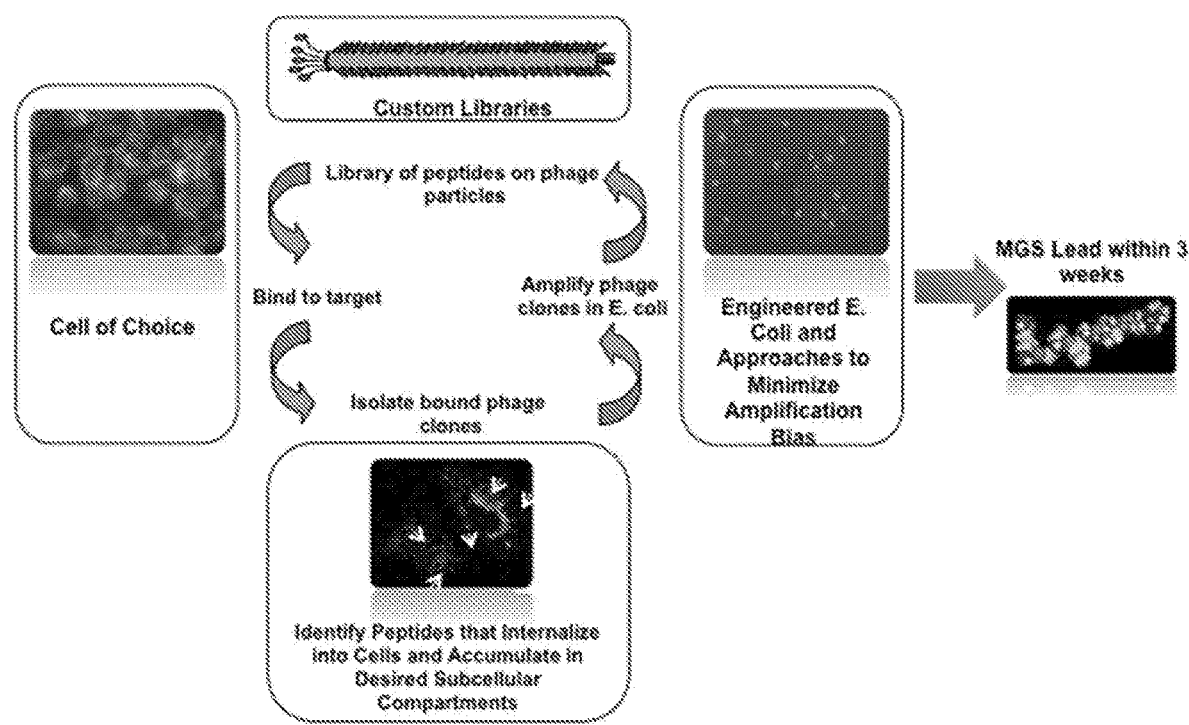
FIG. 2 is a schematic diagram of the FOX-Three Platform. The approach is versatile and has yielded MGSs for many different cell types. The additional selection for subcellular locations further expands the utility of the platform and opens up new therapeutic opportunities for MGSs.

The FOX-Three platform is based on established phage display libraries containing $10^9$-$10^{12}$ candidate peptide-based MGS members that can be rapidly screened against target cells and subcellular systems to identify specifically targeted MGSs (FIG. 2). Peptides are a well-understood class of biomolecule that are readily synthesized by biological processes and through man-made chemical processes. As a result, the power of the FOX-Three platform is demonstrated in its speed and flexibility. It can be applied to any cell type, regardless of knowledge about the molecular features of that cell, producing a lead MGS in 2-4 weeks. Selected peptide-based MGSs are then readily engineered for optimal performance. Table 2 shows MGSs identified using the FOX-Three Technology.

TABLE 2

MGSs identified by FOX-Three Technology

| Indication | Cell Type Targeted | MSG Code and Cellular Location | Payloads Delivered |
|---|---|---|---|
| Carcinomas and Solid Tumors | Non-Small Cell Lung Cancer Cells | MGS_H1299.1_Intracellular<br>MGS_H1299.2_Intracellular<br>MGS_1299.3_Lysosome/Autophagosomes<br>MGS_H2009.1_Golgi<br>MGS_H2009.2_Lysosome<br>MGS_H2009.3_Lysosome<br>MGS_H2009.4_Golgi/ER<br>MGS_H2009.5_ER/Lysosome<br>MGS_H1993.1_Lysosome<br>MGS_H1993.2_Intracellular<br>MGS_H1993.3_Intracellular<br>MGS_H1993.4_Pre-mitotic cells only<br>MGS_H1993.5_Intracellular<br>MGS_H1993.6_Intracellular<br>MGS_H460.1_PlasmaMembrane<br>MGS_HCC15.1_Intracellular<br>MGS_HCC15.2_Intracellular<br>MGS_A549.1_Intracellular<br>MGS_HCC95.1<br>MGS_H1155.1<br>MGS_H1155.2<br>MGS_H66.1 | Monoclonal Antibodies<br>Small molecule therapeutics (doxorubicin, paclitaxel, DM1, auristatin and duocarmycin<br>Fluorophores<br>Nanoparticles (liposomes, micelles, quantum dots, SPIO)<br>Imaging agents (PET, NIR, MR)<br>Peptide and proteins<br>Proteinaceous toxins<br>Antigenic peptides<br>Bead-based capture |
| Lymphoma and Leukemia | Lymphoma Cells | MGS_A20.1_PlasmaMembrane<br>MGS_A20.2_Plasma Membrane<br>MGS_PCM.1_Plasma Membrane | Proteins<br>Fluorophores<br>Bead-based capture |
| Vaccine Development | Dendritic Cells | MGS_XS52.1_Intracellular<br>MGS_XS52.3_Intracellular | Liposomes<br>DNA<br>Protein antigens<br>Fluorophores |
| Diabetes | β-Cells of the Islets of Langerhans | MSG_RII.1<br>MGS_RII.2 | Proteins<br>Radionuclides |
| Pathogen Infected Cells | Mycoplasma Arginine Infected Cells | MGS_MArg.1_Bacterial | Fluorescent dyes<br>Bead-based capture |
| Cardiovascular Disease | Cardiomyocytes | MGS_PCM.1_Intracellular | DNA<br>Fluorophores |

Intracellular indicates that cellular uptake has been confirmed but the exact intracellular compartment has not been determined. MGS with no location information indicated that cellular binding has been confirmed but cellular location not determined.

Figure 3:
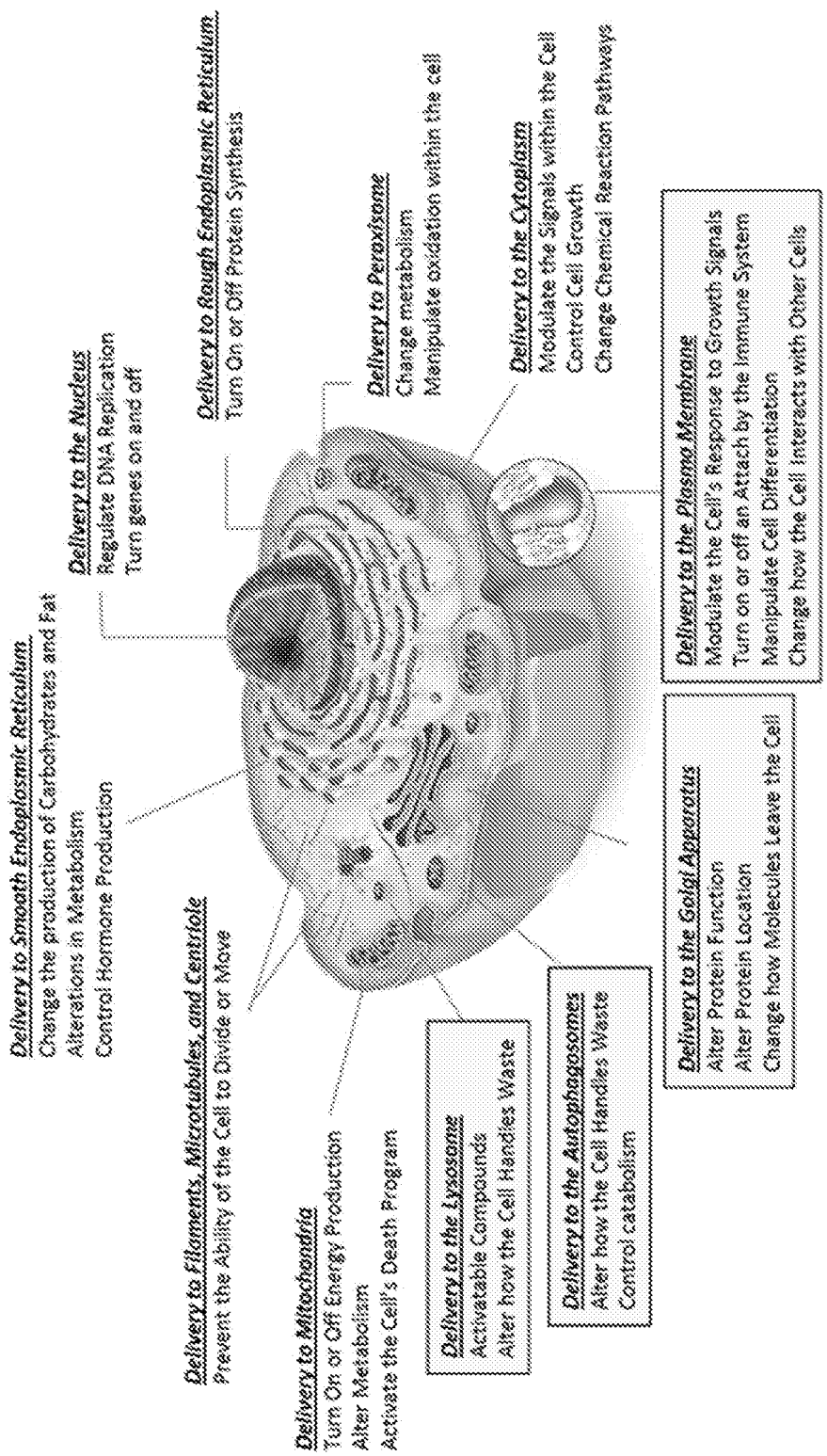
FIG. 3 is a diagram showing examples of cell processes that can be manipulated by targeting therapeutic MAbs to specific subcellular organelles.

The FOX-Three Platform has already been validated for targeting of cells and subcellular components. A number of validated MGSs are in various stages of development (Tables 1 and 2) for a variety of cell targeting systems. Methods of conjugating a variety of payloads to the peptide MGSs have been established without disrupting their targeting ability. Selected MGSs have been demonstrated to deliver drugs, imaging agents, nanoparticles, DNA, and proteins to target cells in culture and in animal models. While cell targeting has been established and there are a number of competing antibody-based technologies for targeting the surfaces of target cells, intracellular MGSs were not previously known. The importance of intracellular targeting is shown in FIG. 3, which shows the complex architecture of a cell. For example, delivery of a MAb intended to bind to proteins involved in DNA replication in the cell nucleus will be therapeutically ineffective if trapped in the Golgi or other locations in the cell. The FOX-Three screening process was recently refined to include subcellular location targeting as a selection criteria. MGSs have been isolated that accumulate in lysosomes, autophagosomes, and Golgi inside cancer cells, as well as target the plasma membrane (FIG. 3). The therapeutic efficacy of MGSs has been demonstrated to be dependent on delivery to the correct subcellular location.

With the wealth of cell types, disease states, intracellular organelles, and payloads that can be delivered, the potential of the FOX-Three platform is vast. A robust platform for creating a 'tool box' of optimized MGSs can be developed that can deliver a focused set of MAbs against select disease cell types and subcellular components. To do this the FOX-Three platform can be used to expand the number of subcellular organelles that can be targeted (FIG. 3). A set of experiments with quantitative milestones can be performed.

In some aspects, synthesis, characterization, and optimization of 3 MGSs that target a non-small lung cancer cell line and accumulate in the lysosome, Golgi, and mitochondria can be studied.

In some aspects, three isolated MGSs can be used to deliver a biologically active antibody intracellularly to the lysosome, Golgi, and mitochondria. Modulation of specific protein targeting in each of these subcellular components can be demonstrated.

In some aspects, at least 5 MGSs that target virally infected cells can be identified. Furthermore, the subcellular locations can be expanded to include lysosome, Golgi, mitochondria, Endoplasmic reticulum, cytoplasm, and nucleus.

The ability to deliver therapeutic MAbs to a specific target cell, and to the right compartment within that cell, can have numerous societal health benefits. MGS-MAb combinations can create a new class of safe and efficacious intracellular acting drugs with the potential to treat heretofore "undruggable" targets. This opens up new therapeutic strategies for the treatment of emerging infectious diseases and bioterrorism, novel therapies for cancer, diabetes, neurological and neurodegenerative diseases and even genetically inherited diseases. MGS-MAb combination drugs can create an entirely new market for this novel drug class, at least as big as the current market size of $70B for MAbs, impacting virtually every disease state and creating a major breakthrough in modern medicine.

The FOX-Three discovers MGSs and offers the rapid development of intracellular targeting human therapeutic antibodies in unprecedented speed to create extremely safe and rapid responses to emerging threats.

The developed FOX-Three MGS tool box can deliver a variety of other payloads. While the delivery of MAbs has been a main focus, it is important to note that MGSs can deliver many different payloads and have other clinical applications (Tables 1 and 2). MGSs can deliver small molecule drugs, imaging agents, nanoparticles, DNA, radionuclides and other proteins. MGSs can be employed for early detection of disease and as companion diagnostics. Early disease detection is often the major determinant of clinical outcome. Companion diagnostics can follow the response to treatment, allowing for rapid changes in treatment, as necessary, saving time and costs. The MGS-therapeutic can be used for targeted therapeutics (small molecule, nucleic acid. Synthetic macromolecules such as polymers, and protein) for a wide variety of disease states, in vitro and in vivo diagnostics, personalized therapies for cancer, intracellular nanoparticle delivery, and innovative immunotherapies.

This technology has the ability to rapidly generate MGS-MAbs that target pathogen infected cells, improving treatment for existing as well as emerging pathogens in weeks versus years. Current technologies are too slow to develop targeting treatments for evolving viruses.

This technology opens up new classes of therapeutics for the treatment of numerous diseases by delivering previously cell-impermeable compounds enabling an entirely new armory for protecting the warfighter This technology provides the ability to detect and neutralize latent intracellular viral infections that may otherwise reactivate or spread/re-spread throughout a community.

This technology can rapidly develop MGSs that can be used in diagnostics and sensor technologies for biological readouts.

B. Example 2

The MGSs can impact treatment of multiple disease and open new therapeutic options. Targeting protein interactions creates a new class of intracellular acting drugs with the potential to treat "undruggable" targets. The therapeutic indications include cancer, emerging infectious diseases and bioterrorism, heart disease, diabetes, fibrosis, neurological and neurodegenerative diseases. The MGSs have a wide applicability and can be utilized to deliver small molecule drugs, imaging agents, nucleic acid and protein delivery, nanoparticles, and cellular therapies.

A small peptidic-MGS delivers a large monoclonal antibody into a cell in vitro and in vivo. Small peptides would not be able to carry a MAb that is almost greater than 60-times its molecular weight. Cells were treated with a MAb alone and no cellular uptake occurred. But when that MAb was conjugated to one of the identified MGS peptides, a 20-4000 fold increase in cellular uptake was seen. The peptide not only delivers a cell impermeable MAb inside the cell-attaching the MAb does not change the peptide's ability to accumulate in the desired subcellular location.

Figure 4A:
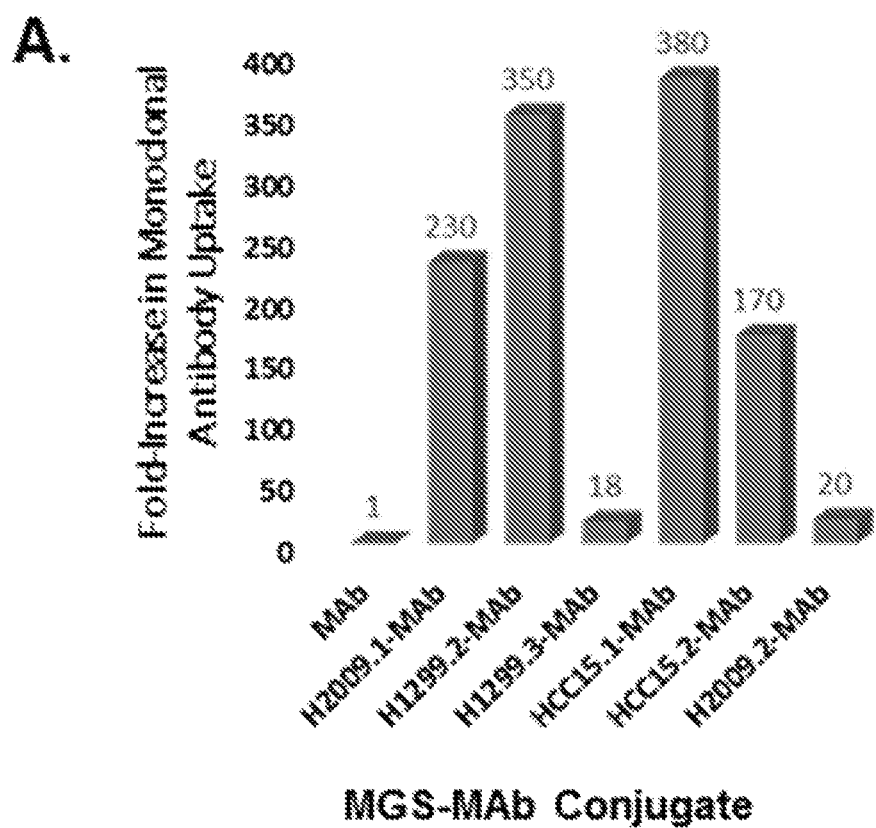
FIGS. 4A, 4B and 4C shows molecular guidance system (MGS) peptides deliver a large monoclonal antibody into a cell in vitro and in vivo. Peptide MGS with a biotin tag ("handle") was coupled to an anti-biotin antibody. The antibody was labeled with a fluorescent tag. Panel A. MGS peptide-antibody was incubated with viable cells in culture. Uptake of the antibody into the cells was determined by flow cytometry and normalized to antibody uptake with no MGS peptide. Panel B. Uptake of the antibody was determined by fluorescent microscopy and is indicated by red "dots" in the left panel. The MGS peptide can deliver the antibody to the desired location. Using a MGS peptide that internalizes and directs cargo to the Golgi apparatus in the cell, an antibody was delivered to that subcellular compartment. Panel C. MGS peptide-Antibody was injected I.V. into a tumor bearing mouse. At set times points, near-infrared imaging was used to determine uptake of the antibody in the tumor.
Figure 4B:
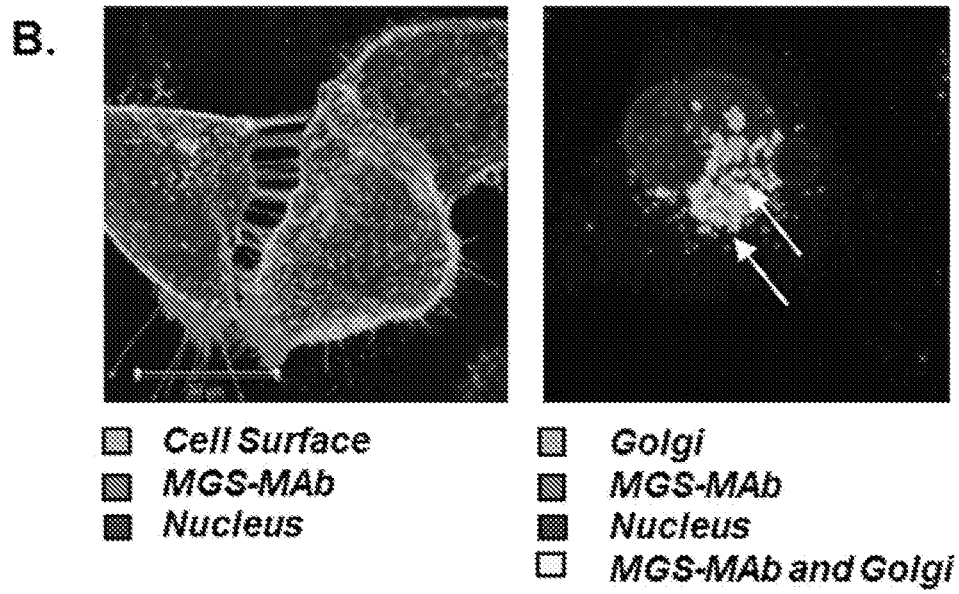
Figure 4C:
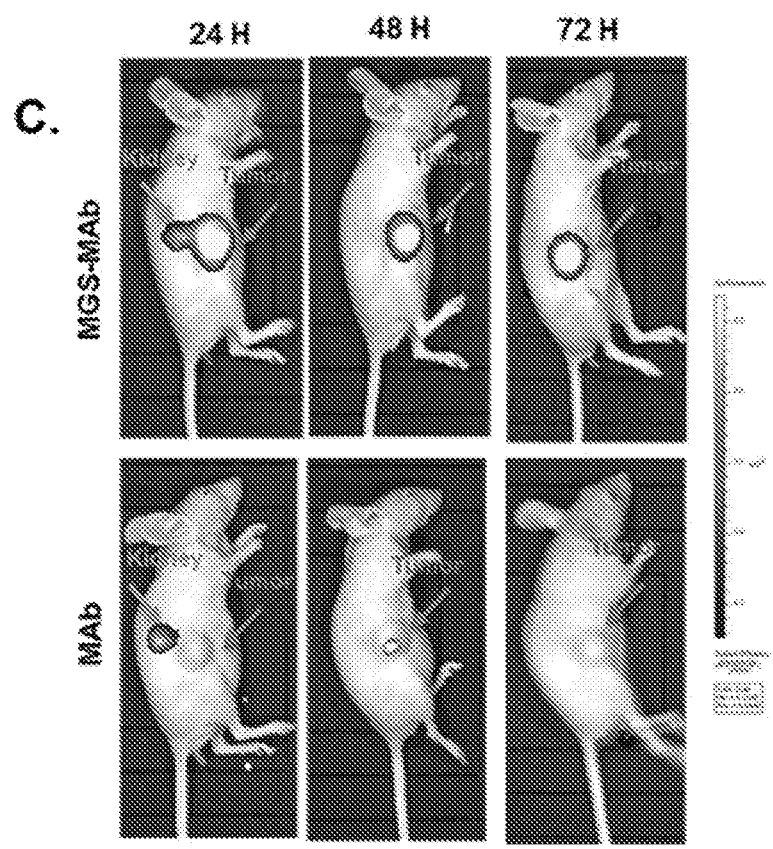
Figure 5:
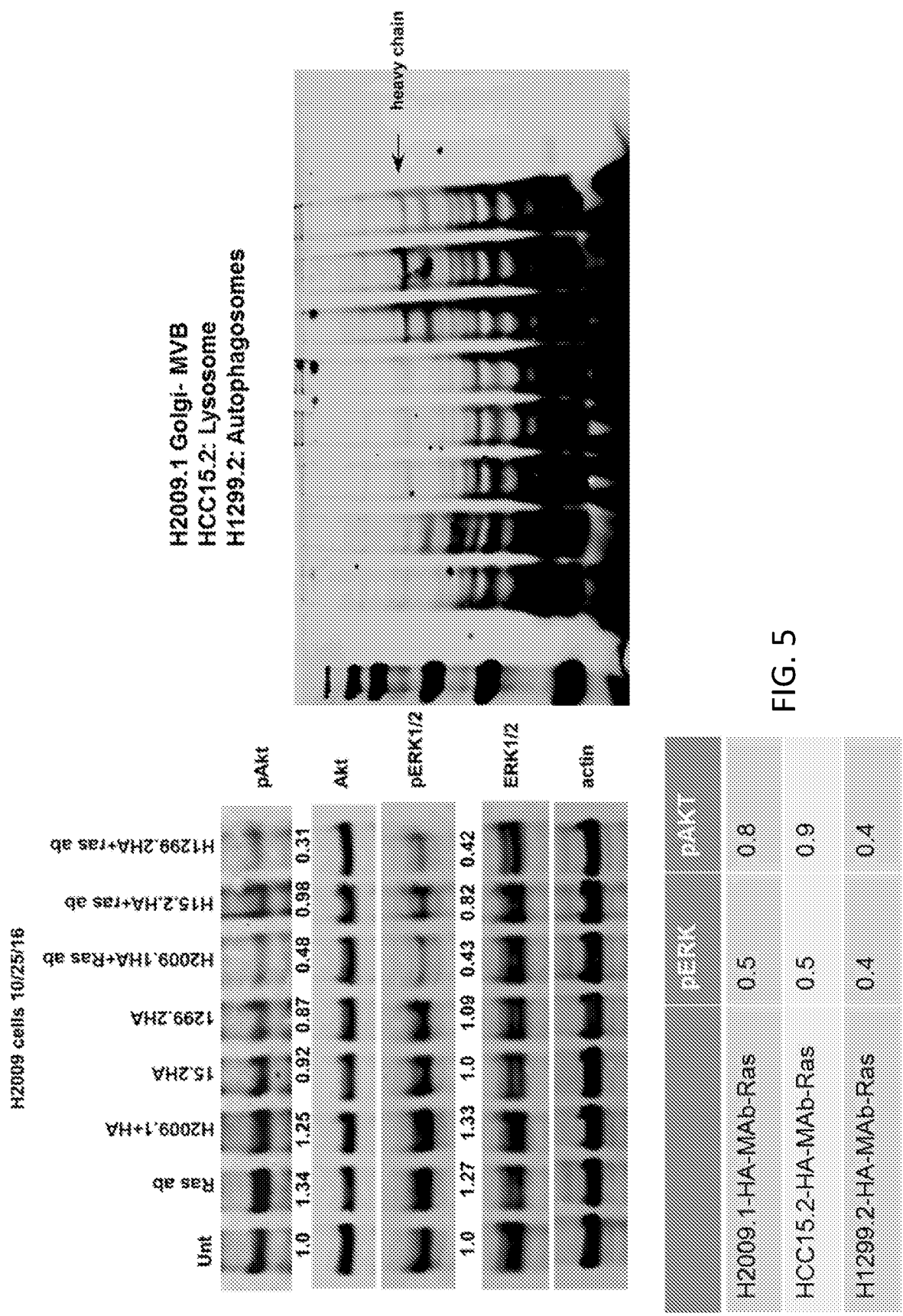
FIG. 5 shows a MGS Peptide-Delivery of Anti-Ras MAb.
Figure 6:
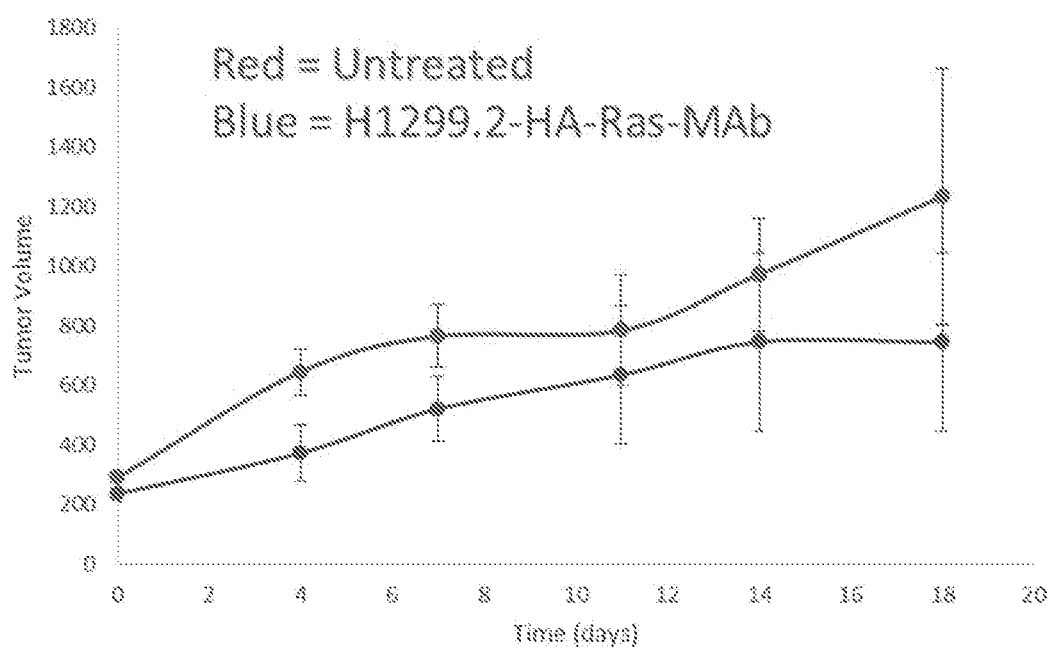
FIG. 6 is a graph showing H2009 Tumor Growth in Nu/Nu Mice treated with H1299.2-HA-Ras-MAb.
Figure 7:
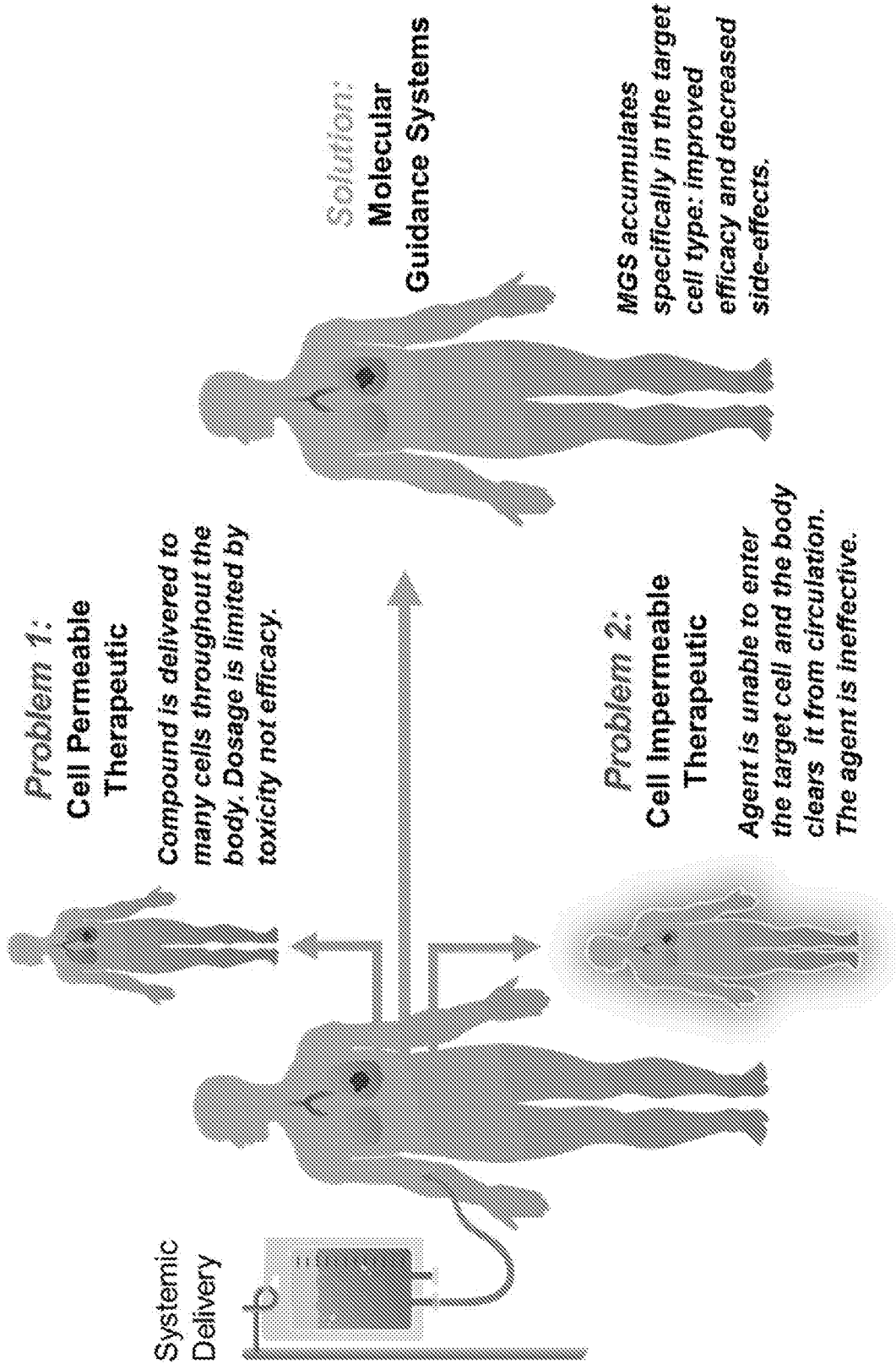
FIG. 7 is a diagram showing Molecular Delivery Systems that Deliver Cargo Intracellularly Solve Two Key Problems that Hinder Drug Development.
Figure 8:
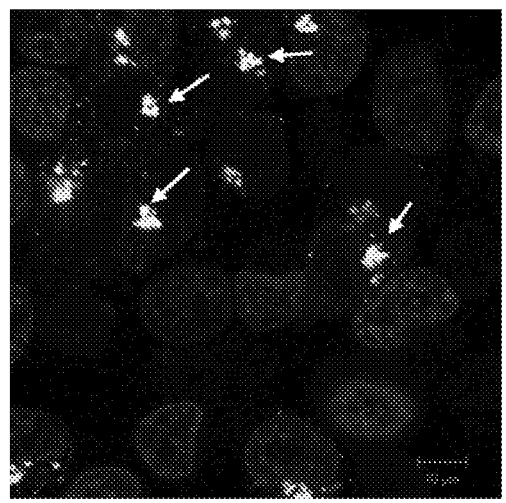
FIG. 8 shows the localization of an MGS peptide disclosed herein.

Peptidic-MGSs can deliver a MAb and increases cellular uptake by 20-380 (FIG. 4A). Peptidic-MGS can deliver a MAb to a discrete subcellular location as dictated by the MGS. (FIG. 4B). Peptidic-MGS can redirect a MAb to a tumor and retain the MAb in the tumor >72 H (FIG. 4C). Tumor uptake is increased 2-4-fold while non-specific tissue (e.g. kidney and liver) uptake is reduced.

Figure 9:
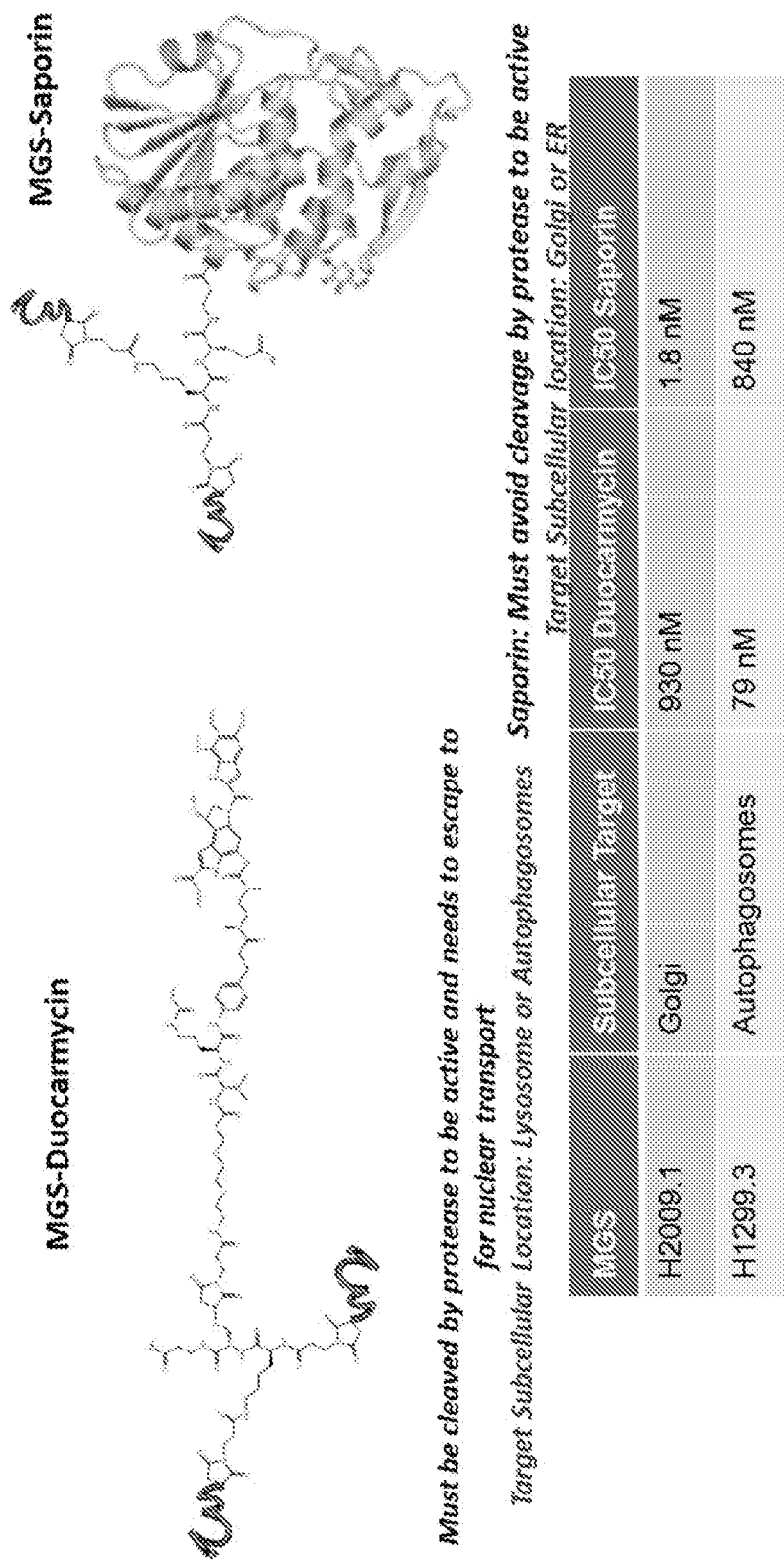
FIG. 9 shows the delivery of an active therapeutic to the desired subcellular location.

Another example of how the peptides (MGSs) can deliver cargo to the correct subcellular location and the importance of this precision delivery, 2 different peptide therapeutic conjugates were tested. The first peptide (MGS) is a Golgi targeting peptide that binds specifically to NSCLC cells (FIG. 9). This peptide (MGS) was conjugated to a duocarmycin, a DNA damaging agent. This conjugate has a linker between the drug and the peptide that must be cleaved by an enzyme found in the lysosome in order to become active and reach the nucleus. However, when the cells are treated with this conjugate, it is virtually nontoxic to these cells, despite the fact that this is an extremely potent drug. This is because this peptide accumulates in the Golgi and is sequestered there.

Peptidic-MGS can deliver cell-impermeable therapeutics (protein toxin, saporin, and a DNA alkylator, duocarmycin) and specifically kill a cancer cell. Subcellular localization dictates the efficacy of the therapeutic. Preliminary data of MGS-Saporin conjugate shows anti-tumor efficacy in an animal.

Figure 10:
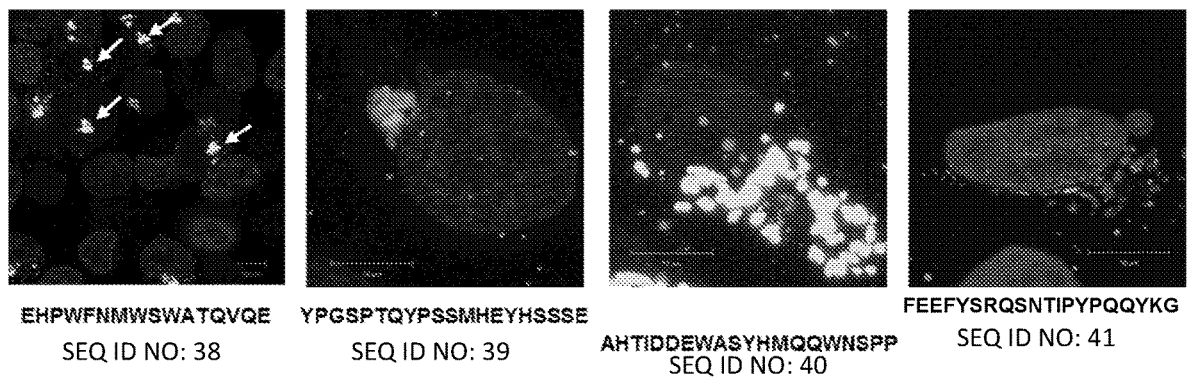
FIG. 10 shows seven MGS peptides that meet affinity and specificity metrics. Peptide sequences listed in the top panel for top to bottom are: SEQ ID NOs: 38, 39, 40, 41, 19,20 and 21.

FIG. 10 shows seven MGS peptides and their subcellular localization compartment. The peptide EHPWFNMWSWATQVQE (SEQ ID NO:38) (H2009.2) has been pushed forward first. The peptide valency has been optimized, it binds to 3 different non-small cell lung cancer cells with minimal binding to normal control cells, it delivers a MAb intracellularly, and effectively delivers a cell impermeable protein-toxin to induce cell death in a cancer cell with a potency of 80 nM.

Figure 11:
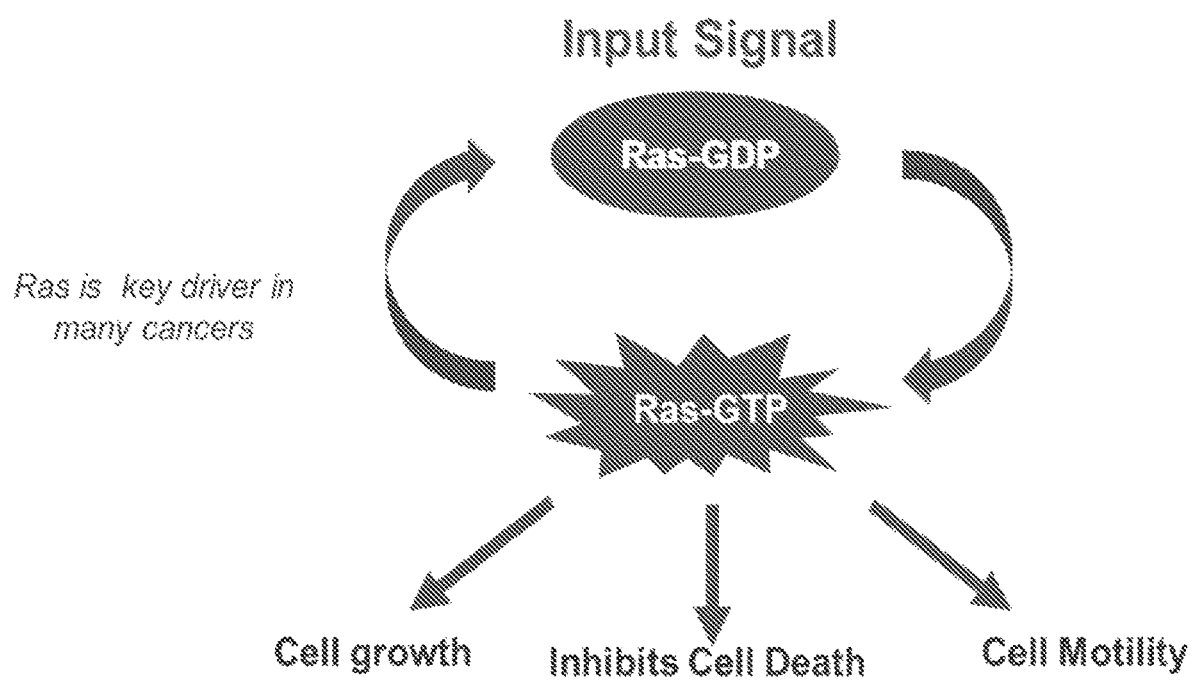
FIG. 11 shows that Ras is a cancer protein that can be targeted with the MGS peptide.
Figure 12:
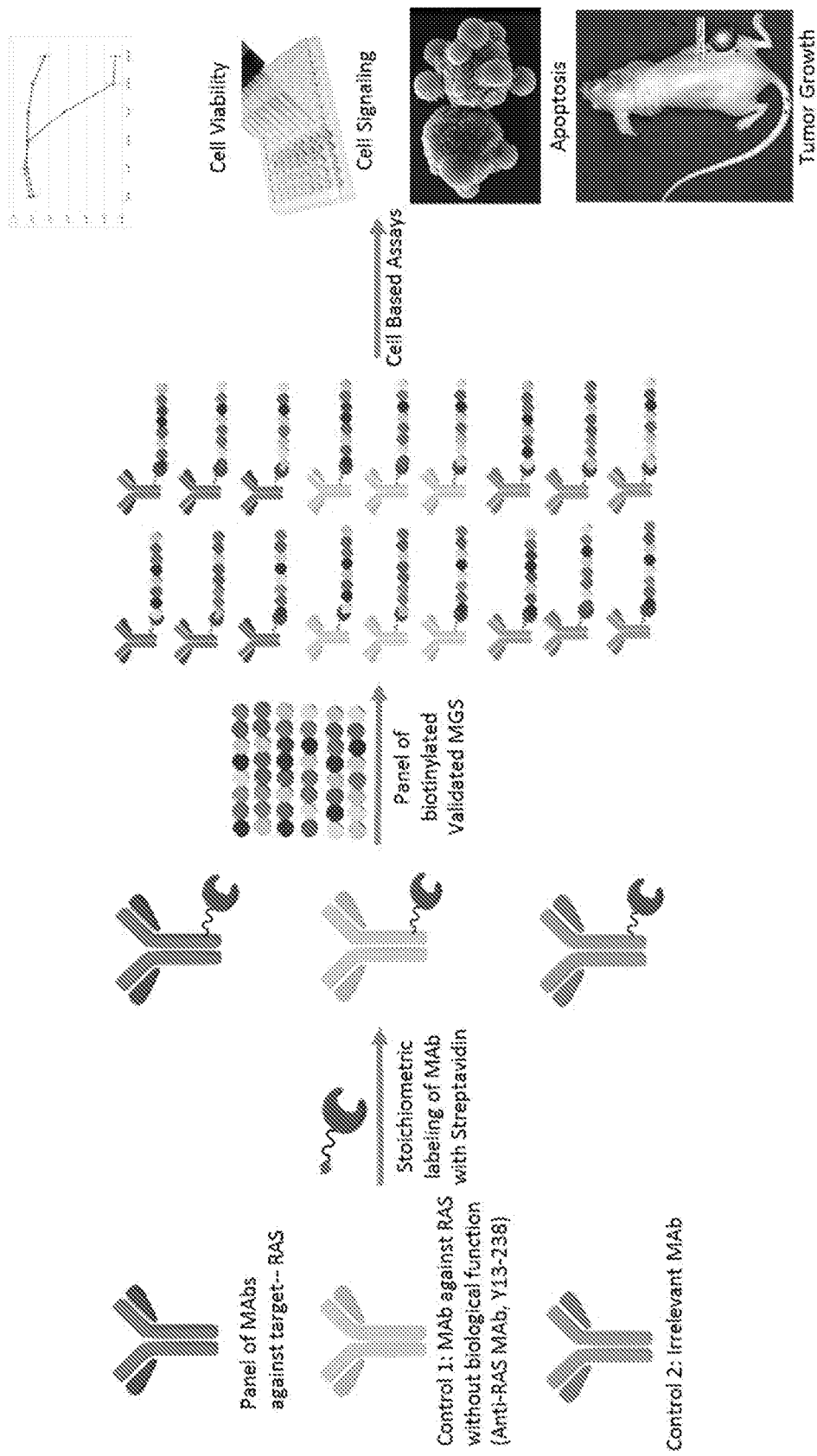
FIG. 12 shows the conjugation optimized for 1 to 1 paring of mAb and MGS peptide.
Figure 13:
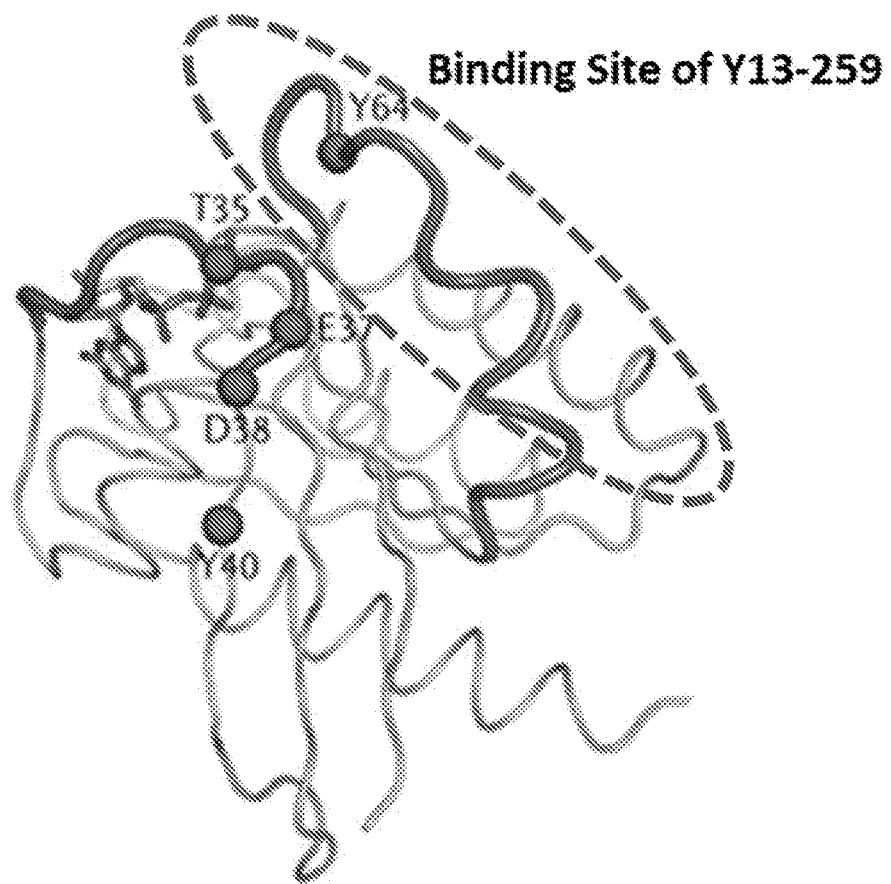
FIG. 13 shows RAS antibody selection of a function blocking anti-RAS monoclonal antibody (Y13-259). The hybridoma was isolated in 1982. It is a rat IgG1 monoclonal antibody that recognizes K-, N-, and H-RAS and binds to both wild-type and mutant RAS. The antibody binds amino acids in the switch II region of RAS. The Y13-259 scFv fragment was cloned. The antibody blocks RAS mitogenic activity in cell based assays via electroporisis.
Figure 14:
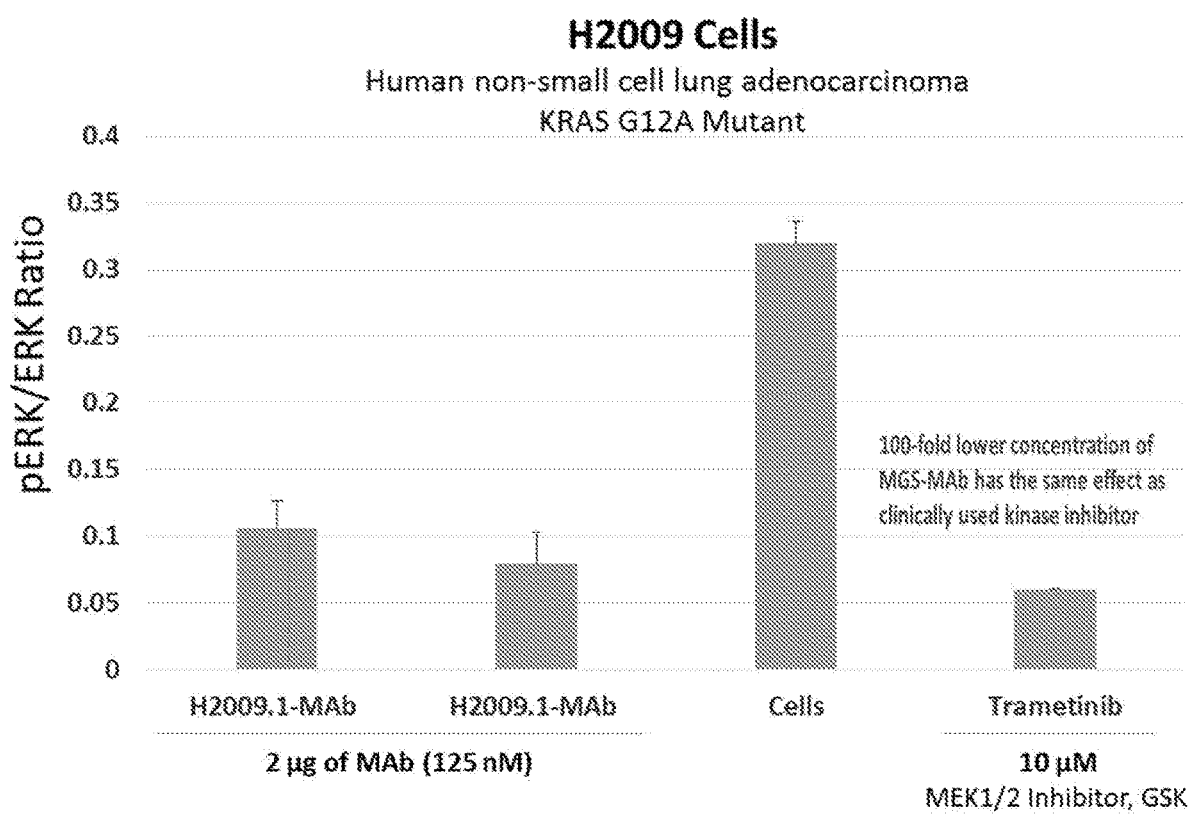
FIG. 14 shows that the MGS peptide, H2009.1-Y13-259 reduces activation of a downstream target of KRAS. The limitations of Trametinib (and other downstream kinase inhibitors) are: only disrupts one of RAS's many pathways, toxicity, drug resistance almost always arises within 6-18 months, and cross-talk between RAS-mediated pathways results in compensation.
Figure 15:
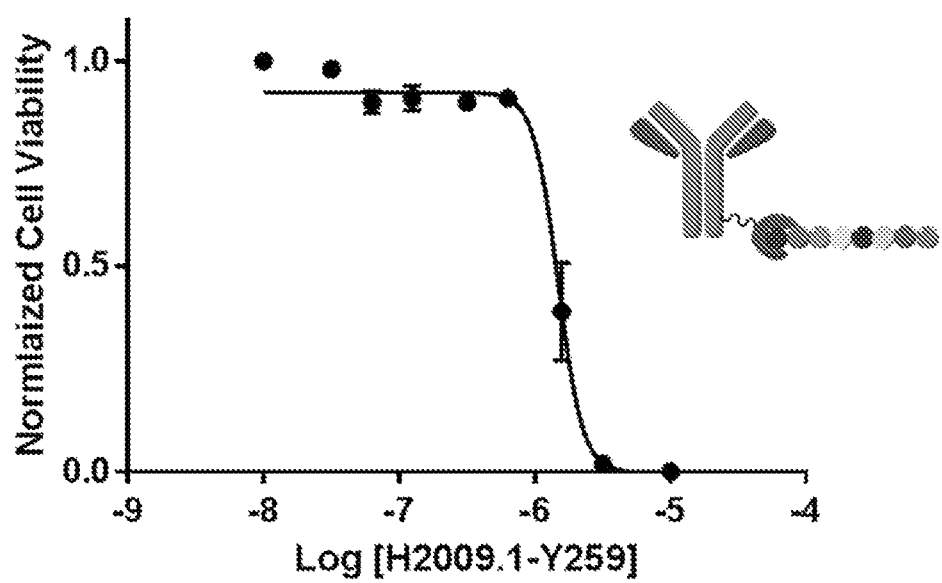
FIG. 15 shows that the MGS peptide, H2009.1-Y13-259 is cytotoxic to a non-small cell lung cancer cell line with an $IC_{50}$ of 1.5 μM. Anti-RAS antibody was coupled to the MGS peptide, H2009.1 via a biotin-streptavidin conjugation. Varying concentrations were incubated with H2009 cells, a human non-small cell lung cancer cell line. Cell viability was measured at 72 H using a cell TiterGlo assay.
Figure 16:
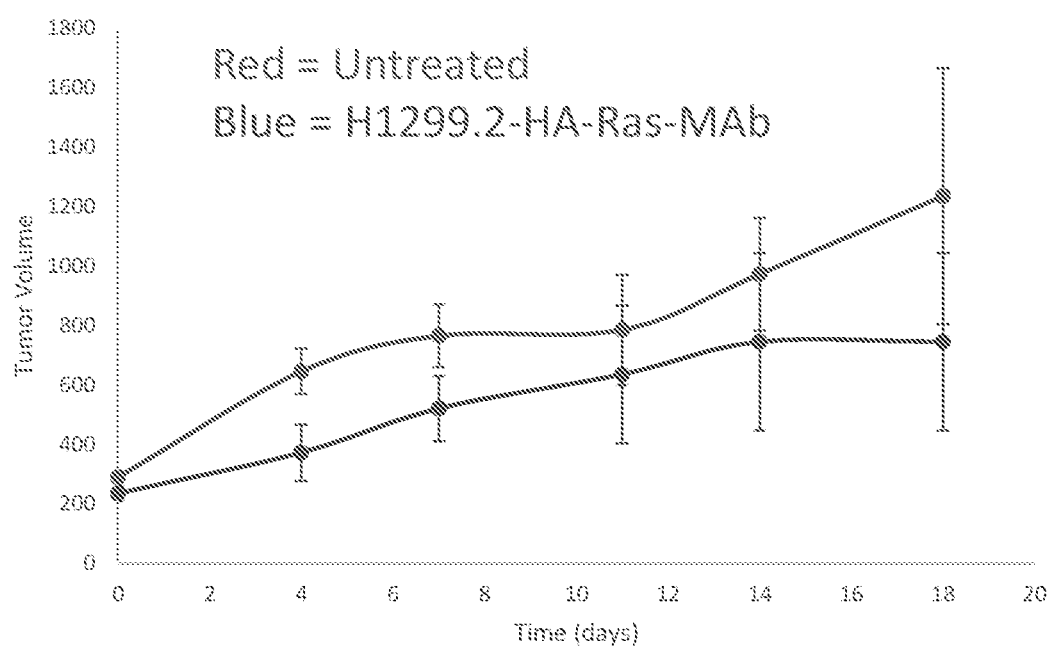
FIG. 16 shows H2009 tumor Growth in Nu/Nu mice treated with the MGS peptide, H1299.2-HA-Ras-MAb.

FIG. 11 shows that Ras is a critical node in cancer proliferation and has been challenging to drug. MAb therapeutic approaches to treating Ras would lower total levels of Ras in the cell, change the cellular location to prevent activation, and hold Ras in the inactive state.

Figure 17:
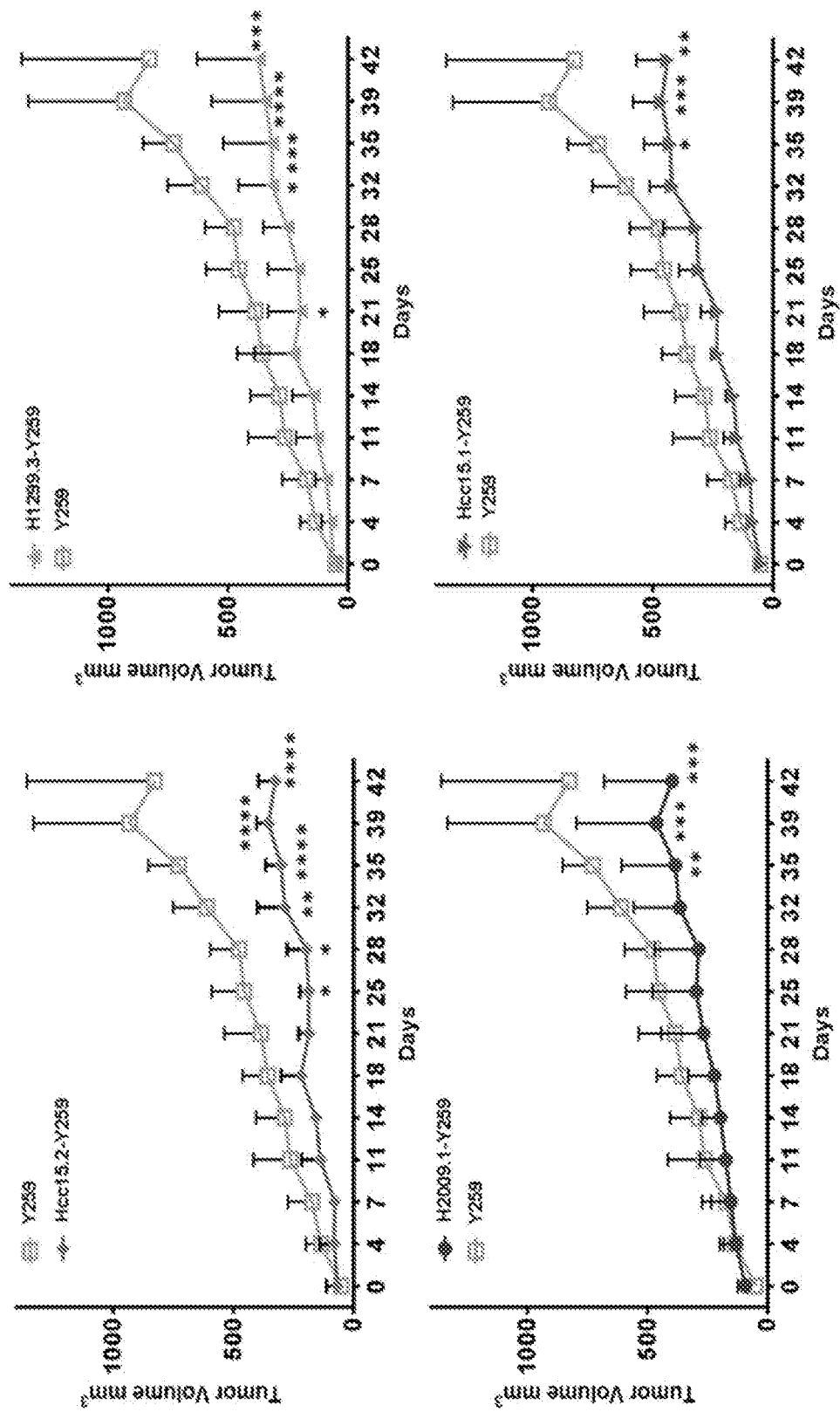
FIG. 17 shows targeting of intracellular protein-protein interactions using an MGS peptide-Ras mAb. H358 Human Lung Cancer Subcutaneous Tumors were used. KRAS G12C Mutation. IV Injections of 25 μg MAb per mouse at days 0, 7, 14, and 25.
Figures 19A, 19B, 19C:
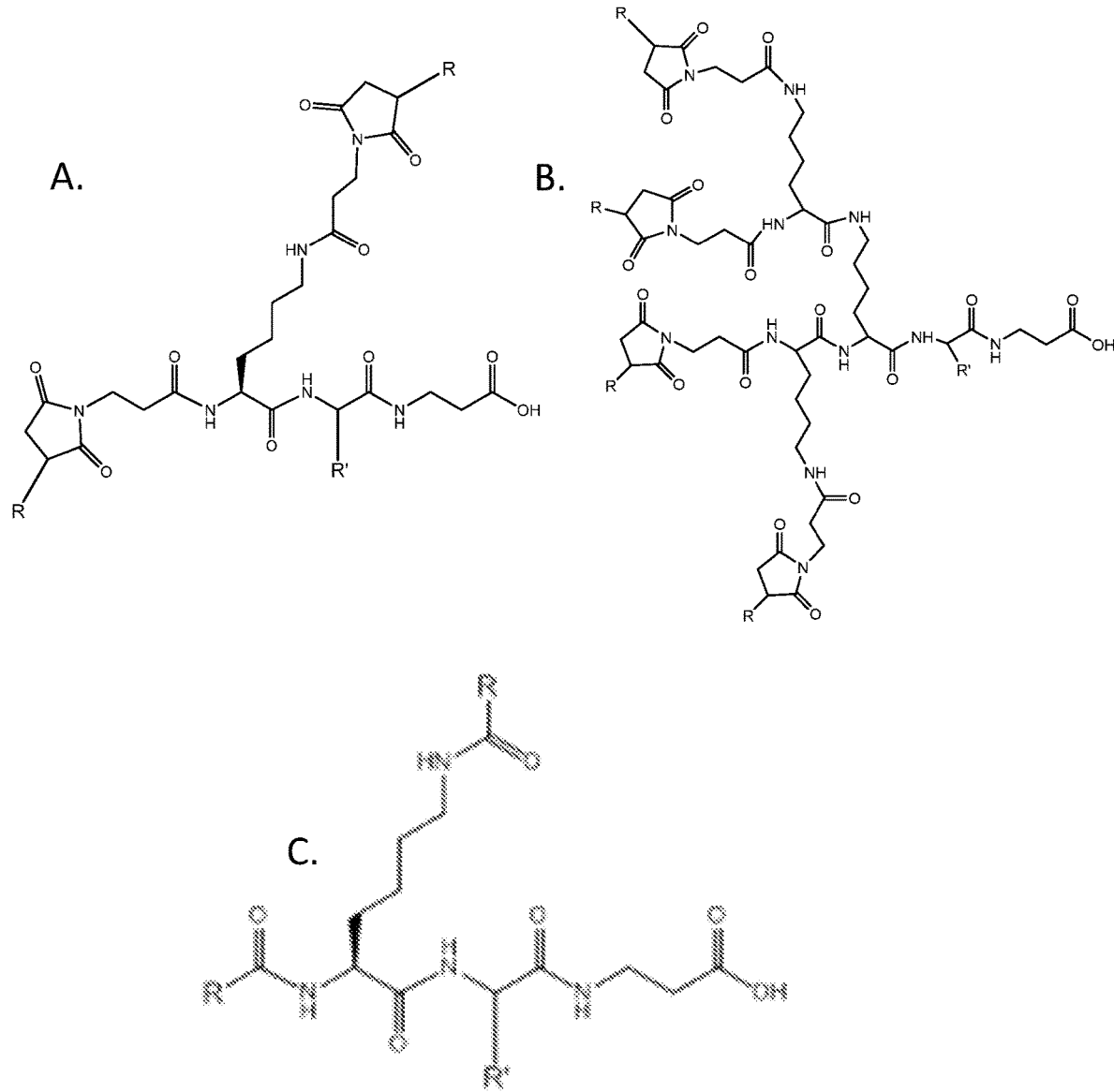
FIGS. 19A, 19B, and 19C show structures of multimerization scaffolds. 19A shows a dimer core available for site-specific maleimide linkage of 2 MGS peptides and available linkage of a cargo molecule using an additional reacting group (R'). 19B shows a tetramer core available for site-specific maleimide linkage of 4 MGS peptides and available linkage of a cargo molecule using an additional reacting group (R'). 19C shows prototype dimeric cores with separate chemical reactive groups, R, for linking 2 MGS peptides and R', for linking to cargo. Available reactive groups include but are not limited to azido-, aldehyde, hydrazide, esters, and others.

FIG. 17 shows reduction of tumor growth compared to no treatment or treatment with MAb alone. No gross toxicities were observed.

Figures 20A, 20B, 20C:
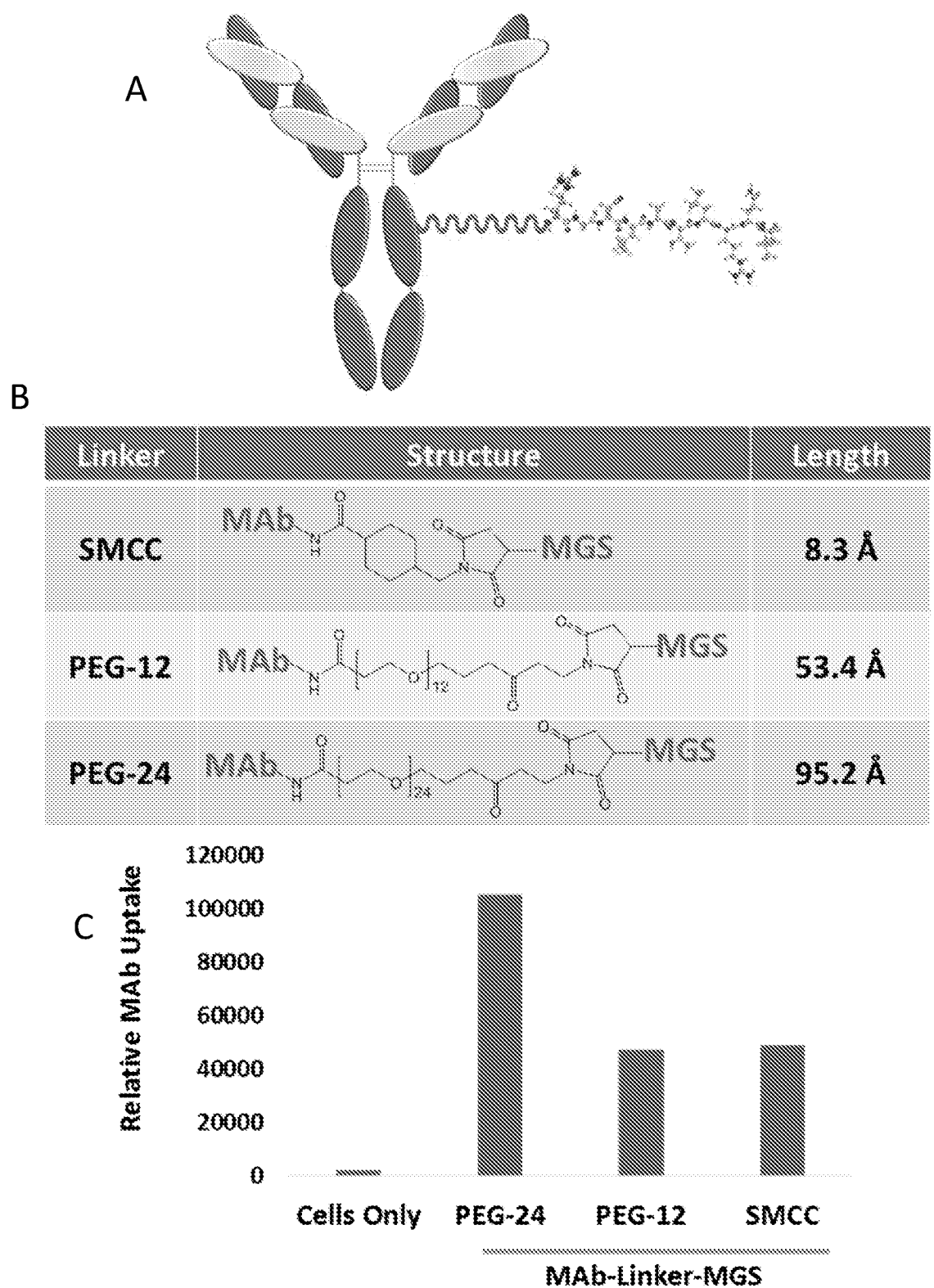
FIGS. 20A, 20B, and 20C show the direct conjugation of a MGS peptide to an antibody and its intracellular delivery.
Figure 21:
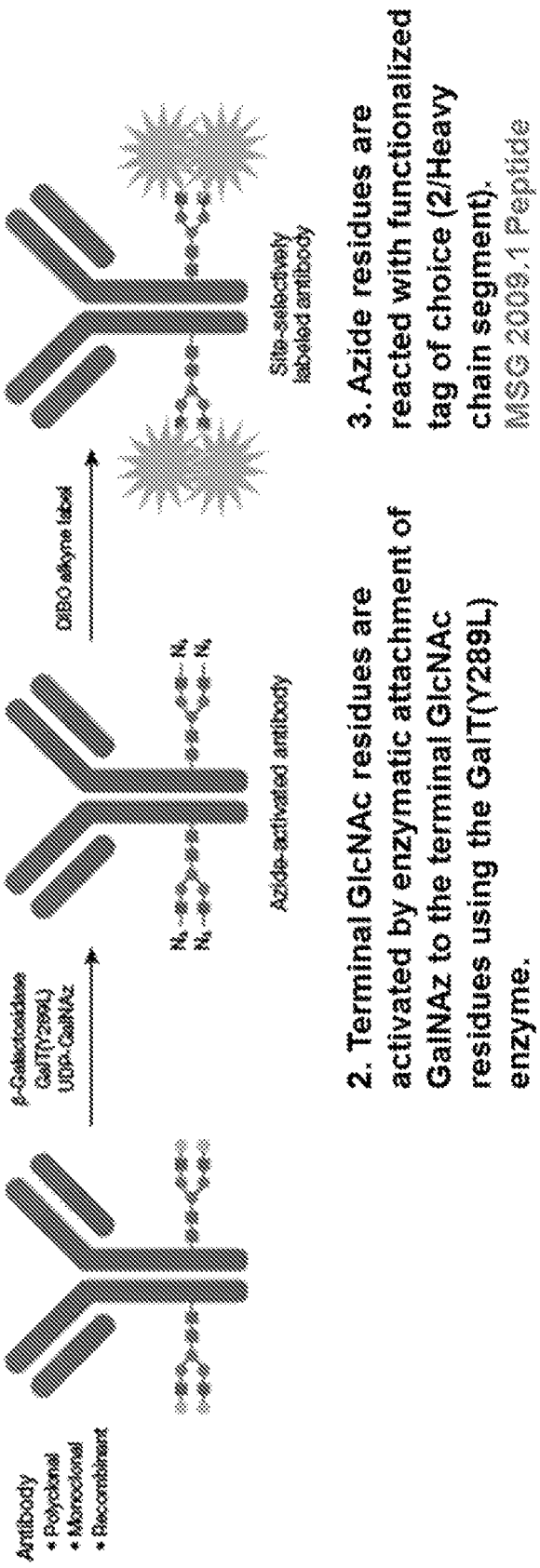
FIG. 21 shows the SiteClick method for peptide conjugation to an antibody.
Figure 22:
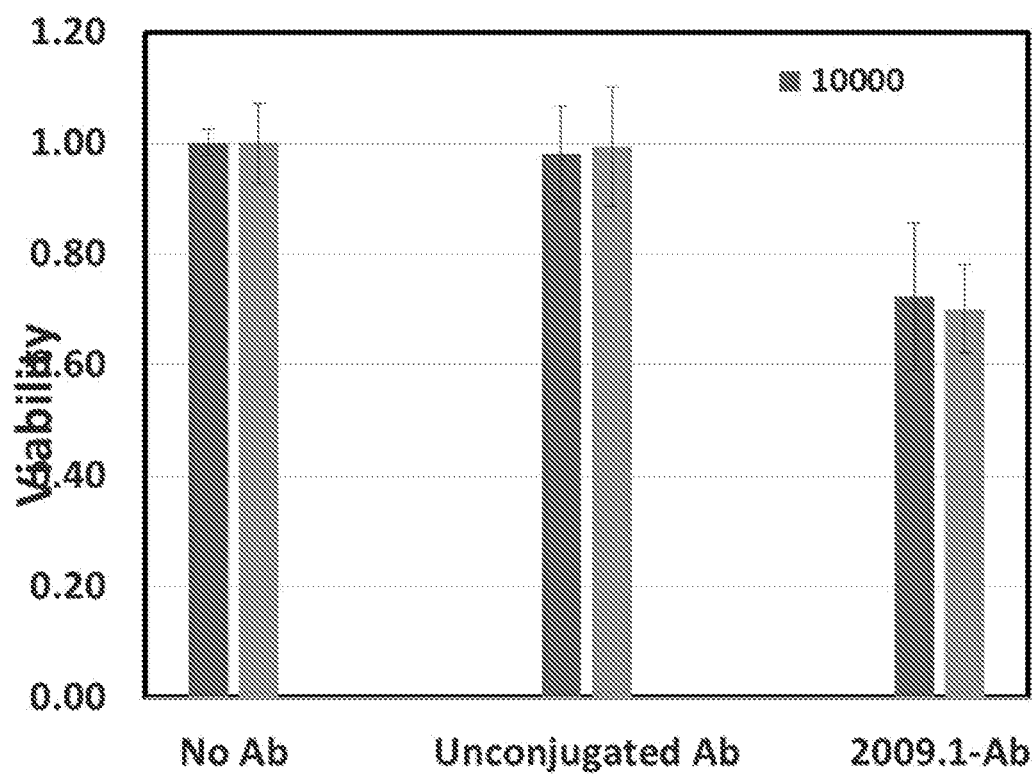
FIG. 22 shows H358 cells exhibit reduced viability after MSG 2009.1-Anti-Ras Ab treatment. 1 treatment, 50 nM Ab, 72 hr continuous exposure.

FIG. 20 shows that direct conjugation does not disrupt the MGS's ability to mediate cellular uptake. A longer linker between an MGS and MAb increases uptake in target cells. Bi-functional linkers with the same chemically reactive groups were used to form conjugates between a MAb (NHS ester chemistry) and the MGS-peptide (maleimide chemistry). SMCC has no PEG spacer while the PEG-12 and PEG-24 molecules have shorter or longer PEG repeats between the chemically reactive groups which enhance the ability of the MGS-peptide to interact with its cellular receptor without steric hinderance from the MAb protein. As demonstrated, the PEG-24 spacer enabled higher MAb-MGS conjugate uptake than the 2 conjugates with shorter spacer arms.

Figure 23:
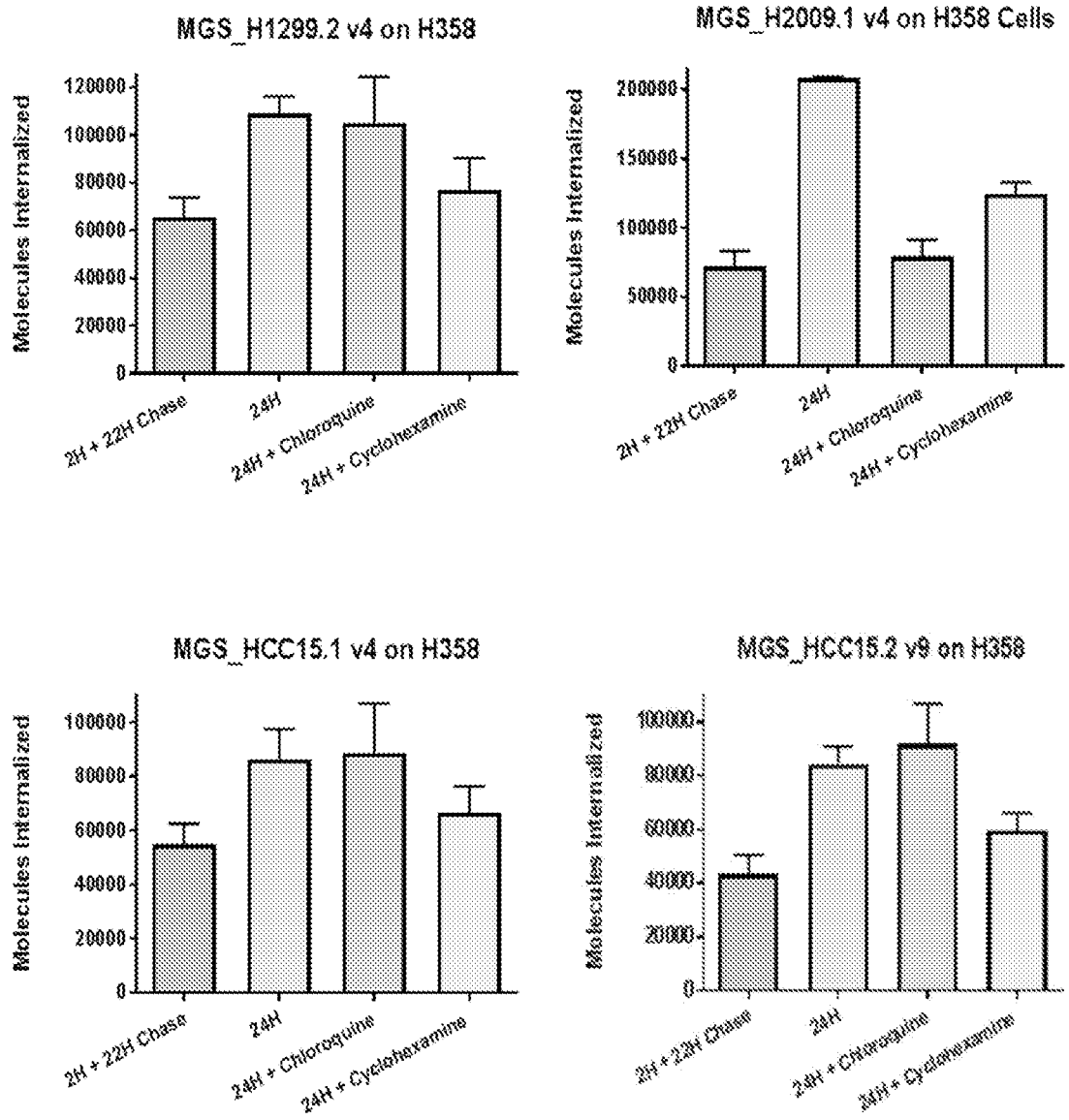
FIG. 23 shows the role of receptor recycle vs new receptor synthesis in MGS internalization.
Figure 24:
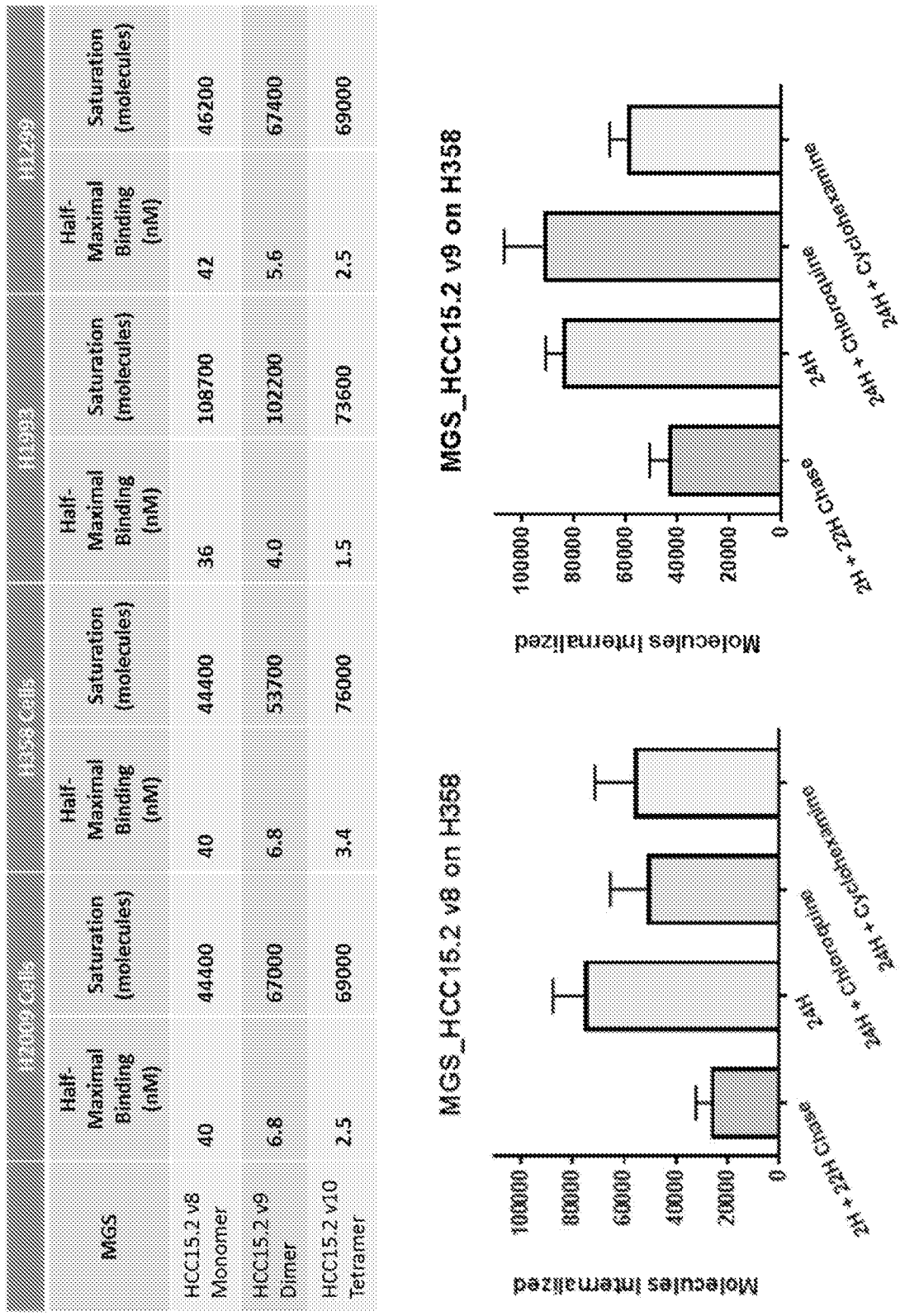
FIG. 24 summarizes key kinetic features of cellular uptake of 3 distinct valency versions of peptide HCC15.2 (monomer, dimer, and tetramer) on 4 different NSCLC cell lines illustrating significant enhancement of peptide affinity with dimerization but modest improvement upon tetramerization. Further experiments suggest that differences in MGS-peptide valency can alter the cells ability to recycle the peptide receptor allowing additional control of cargo uptake.

FIG. 23 demonstrates how some MGS peptides bind to a cellular receptor that is recycled and some MGS peptides bind to a cellular receptor that needs to be newly synthesized. MGS_H2009.1 v4 binds to a cellular receptor that is rapidly recycled back to the cell surface where it can shuttle in another molecule of MGS. MGS_H1299.2 v4, HCC15.1 v4, and HCC15.2 v8 bind to a cellular receptor that is primarily degraded upon internalization and new receptor synthesis occurs in order to internalize more MGS.

The cellular receptor for MGS_H1299.2 v4 is EphA2. The following results were obtained during a study on EphA2. Reduction of EphA2 in cells abrogates MGS_H1299.2 V4 binding. Increasing EphA2 in cells increases MGS_H1299.2 V4 binding. MGS_H1299.2 V4 binds EphA2 from lysed cells and binds to purified EphA2: $K_d$ 3.2 nM. EprhrinA1 and MGS_H1299.2 V4 compete for binding. Lastly, MGS_H1299.2 V4 induces EphaA2 internalization and co-localizes with the receptor in lysosome.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

Those skilled in the art will recognize, or be able to ascertain using no more than routine experimentation, many equivalents to the specific embodiments of the method and compositions described herein. Such equivalents are intended to be encompassed by the following claims.

What is claimed is:

1. A composition comprising an antibody conjugated to one or more molecular guidance system (MGS) peptides, directly or via a linker, wherein the one or more MGS peptides are selected from the group consisting of SEQ ID NOs: 2, 3, 20-22, and 38-41.

2. The composition of claim 1, wherein the antibody targets an intracellular target.

3. The composition of claim 1, wherein the antibody is a monoclonal antibody.

4. The composition of claim 3, wherein the monoclonal antibody is an anti-Ras monoclonal antibody.

5. The composition of claim 1, wherein the one or more MGS peptides consists of SEQ ID NO: 38.

6. The composition of claim 1, wherein the one or more MGS peptides localize to an intracellular target selected from the lysosome, golgi apparatus, endoplasmic reticulum, cytoplasm, or nucleus.

7. The composition of claim 1, wherein the antibody is conjugated to the one or more MGS peptides via a linker.

8. The composition of claim 7, wherein the linker comprises polyethylene glycol (PEG).

9. A molecular guidance system (MGS) peptide selected from the group consisting of SEQ ID NOs: 2, 3, 20-22, and 38-41.

10. A method of targeting an intracellular target in a cell in vitro or in a subject, comprising contacting the cell with or administering to the subject a composition according to claim 1, wherein the antibody targets an intracellular target.

11. The method of claim 10, wherein the intracellular target is the lysosome, golgi apparatus, endoplasmic reticulum, cytoplasm, or nucleus.

12. A method of treating a subject having a disease in need thereof comprising administering to the subject in need thereof an effective amount of the composition of claim 1, wherein the antibody targets an intracellular target involved in the disease process.

13. The method of claim 12, wherein the subject in need thereof has an infectious disease, cancer, diabetes, a neurological or neurodegenerative disease, a genetically-inherited disease, or has been exposed to a bioterrorism agent.

* * * * *